United States Patent [19]
Fritz et al.

[11] Patent Number: 5,882,924
[45] Date of Patent: Mar. 16, 1999

[54] VECTORS FOR THE GENETIC SELECTION OF LIGAND BINDING PROTEINS IN MICROORGANISMS BY MEANS OF SIGNAL TRANSDUCTION

[75] Inventors: Hans-Joachim Fritz; Frank Hennecke; Harald Kolmar, all of Göttingen, Germany

[73] Assignee: Behringwerke Aktiengesellschaft, Marburg, Germany

[21] Appl. No.: 956,047

[22] Filed: Oct. 22, 1997

Related U.S. Application Data

[63] Continuation of Ser. No. 257,669, Jun. 8, 1994, abandoned.

[30] Foreign Application Priority Data

Jun. 10, 1993 [DE] Germany .......................... 43 19 296.3

[51] Int. Cl.$^6$ .......................... C12N 15/11; C12N 15/70; C12Q 1/68
[52] U.S. Cl. .......................... 435/320.1; 435/6; 536/23.4; 536/23.5
[58] Field of Search .................. 435/320.1, 6; 536/23.5, 536/23.1, 23.4

[56] References Cited

U.S. PATENT DOCUMENTS 5,521,066  5/1996  Menzel et al. .......................... 435/7.2

OTHER PUBLICATIONS

Kolmar et al., "Dimerization of Bence Jones proteins: Linking the rate of transcription from an *Escherichia coli* promoter to the association constant of REIv", Biol. Chem. Hoppe–Seyler 375: 61–70, Jan. 1994.

B.A. Irving et al.; The Cytoplasmic Domain of the T Cell Receptor Chain is Sufficient to Couple to Receptor–Associated Signal Transduction Pathways; Cell, vol. 64 (1991) ; pp. 891–901.

A. K. Wegener et al.; The T Cell Receptor /CD3 Complex is Composed of at Least Two Autonomous Transduction Modules; Cell, vol. 68 (1992) ;pp. 83–95.

F. Hennecke et al.; A Transcriptional Signal Derived from the Dimerization of Immunoglobulin Fragments located in the Periplasmic Space of *E. coli*; Biological Chemistry Hoppe–Seyler, vol. 374, No. F109 (1993) ; pp. 798.

Harald Kolmar et al., "General Mutagenesis/Gene Expression Procedure for the Construction of Variant Immunoglobulin Domains in *Escherichia coli*," Journal of Mol. Biol., vol. 228, (1992) pp. 359–365.

Ludger Diederich, et al., "New Cloning Vectors for Integration into the λAttachment Site attB of the *Escherichia coli* Chromosome, "Plasmid, vol. 28, (1992) pp. 14–24.

Claude Parsot et al., "Expression of the *Vibrio Cholerae*-Gene Encoding Aldehyde Dehydrogenase Is under Control of ToxR, the Cholera Toxin Transcriptional Activator, " Journal of Bacteriology, vol. 173, (1991) pp. 2842–2851.

Hennie R. Hoogenboom et al., "Multi–subunit proteins on the surface of filamentous phage; methodologies for displaying antibody (Fab) heavy and light chains, "Nucleic Acids Research, vol. 19, (1991) pp. 4133–4137.

Pedro M. Alzari et al., "Three–dimensional structure determination of an anti–2–phenyloxazolone antibody: the role of somatic mutation and heavy/light chain pairing in the maturation of an immune response, " The EMBO Journal, vol. 9, (1990) pp. 3807–3814.

Virginia L. Miller et al., "*Cholera Toxin* Transcriptional Activator ToxR Is a Transmembrane DNA Binding Protein, " Cell, vol. 48, (1987) pp. 271–279.

Hiroshi Inouye et al., "Signal Sequence of Alkaline Phosphatase of *Escherichia coli*, "Journal of Bacteriology, vol. 149, (1982) pp. 434–439.

Shau–Ping Lei et al., "Characterization of the *Erwinia cartovora pelB* Gene and Its Product Pectate Lyase, " Jouranl of Bacteriology, vol. 169, (1987) pp. 4379–4383.

Otto EPP et al., "Crystal and Molecular Structure of a Dimer Composed of the Variable Portions of the Bence–Jones Protein REI, " Eur. J. Bioochem, vol. 45, (1974) pp. 513–524.

*Primary Examiner*—Jasemine C. Chambers
*Assistant Examiner*—Scott D. Priebe
*Attorney, Agent, or Firm*—Finnegan, Henderson, Farabow, Garrett & Dunner, L.L.P.

[57] ABSTRACT

The invention relates to a process for the genetic selection in microorganisms of proteins which are capable of ligand binding, in which process a protein which is capable of ligand binding is presented extracytoplasmically and the signal of the ligand binding is passed on by signal transduction to the biosynthetic machinery of the micoorganism for the purpose of expressing a detectable and/or selectable function. In addition to this, the patent discloses microorganisms which are suitable for use in this process, as well as replicons and processes for their preparation.

2 Claims, 4 Drawing Sheets

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTGTGTGATA CGAAACGAAG CATTGGATCC TAGAAGTGAA ACGGGGTTTA CCG    53

( 2 ) INFORMATION FOR SEQ ID NO:2:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTTTTCCCAG TCACGACGAC GTTGTAAAAC GACAGAATCT GCCCGATATA ACTTATC    57

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAGCACGTTG TAGTACTACC TTTACCATAT A    31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGGGTCATAC CGATCCCGTT ATCCGAAATG G    31

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGACGGTACC TGCAGCGTTA GGGGTTTAAA GCTGGATTG    39

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CATCTGGATA TCCGTTAGGG GTTTAAAGC    29

(2) INFORMATION FOR SEQ ID NO:7:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAGCGAGTCG ACTACGTACA GCTGGTGGAG CTTGGGGAG GCTTTGTGCA GCCTGGAGGG    60

TCCCGG    66

(2) INFORMATION FOR SEQ ID NO:8:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AATTTGGGAT CCGCCACCGC CAGAGCCACC TCCGCCTGAA CCGCCTCCAC CTGAGGAGAC    60

GGTGACCAGG GTCCCTTGGC CCC    83

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGTGGCGGAT CCCAAATTGT TCTCACCCAG TCTCCAG    37

( 2 ) INFORMATION FOR SEQ ID NO:10:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGCGGTTCTA GATTATCACC GTTTCAGTTC AAGCTTGGTC CCAGCACCG     49

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GTCTGCATAG TAGATAGTAC TACTGCCACT AC     32

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GACTGGTCAT CTGCAGGAAC AGGGTGTTCT TGGG     34

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GGTCATGGTG ACTTTCTCCC CTGGAG     26

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GGATGTGTCA TATGTCCAGC GCTTGGGGGA GGTG     34

( 2 ) INFORMATION FOR SEQ ID NO:15:

( i ) SEQUENCE CHARACTERISTICS:

(A) LENGTH: 79 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:15:

GAGAACAATT TGGGCCATGG CTGGTTGGGC AGCGAGTAAT AACAATCCAG CGGCTGCCGT    60

GATATCTGAG GAGACGGTG    79

(2) INFORMATION FOR SEQ ID NO:16:

(i) SEQUENCE CHARACTERISTICS:
(A) LENGTH: 80 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:16:

CAGCGGCTGC CGTAGGCAAT AGGTATTTCA TTATGACTGT CTCCTTGAAA TAGAATTCGC    60

ATTATCATGA GGAGACGGTG    80

(2) INFORMATION FOR SEQ ID NO:17:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:17:

TTTGAATTCA TTTGTACATG GAGAAAATAA AGTGAAAC    38

(2) INFORMATION FOR SEQ ID NO:18:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:18:

GACTGGGTGA GAACAATTTG GGCTTTTGTC ACAGGGGTAA AC    42

(2) INFORMATION FOR SEQ ID NO:19:

(i) SEQUENCE CHARACTERISTICS:
(A) LENGTH: 36 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:19:

GAACTGAAAC GGTGATAAGA ATTCATTTGT ACATGG    36

(2) INFORMATION FOR SEQ ID NO:20:

(i) SEQUENCE CHARACTERISTICS:
(A) LENGTH: 39 base pairs

33

-continued ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CCAAGCTCCA CCAGCTGTAC ATCGGCTTTT GTCACAGGG    39

( 2 ) INFORMATION FOR SEQ ID NO:21:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

GAATCTAGAT TATCATGAGG AGACGGTG    28

( 2 ) INFORMATION FOR SEQ ID NO:22:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

ACAGTCGACG ATATCGTTCT CACCCAGTCT CC    32

( 2 ) INFORMATION FOR SEQ ID NO:23:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

CATCTGGATA TCCTACCAAT GCTTAAT    27

( 2 ) INFORMATION FOR SEQ ID NO:24:

( i ) SEQUENCE CHARACTERISTICS:
( A ) LENGTH: 738 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..720
( D ) OTHER INFORMATION: /note= "Molecule 1-720 encodes a peptide."

( x i ) SEQUENCE DESCRIPTION: SEQ ID NO:24:

```
CAG  CGA  GTC  GAC  TAC  GTA  CAG  CTG  GTG  GAG  CTT  GGG  GGA  GGC  TTT  GTG    48
Gln  Arg  Val  Asp  Tyr  Val  Gln  Leu  Val  Glu  Leu  Gly  Gly  Gly  Phe  Val
 1                 5                      10                      15

CAG  CCT  GGA  GGG  TCC  CGG  AAA  CTC  TCC  TGT  GCA  GCC  TCT  GGA  TTC  ACT    96
Gln  Pro  Gly  Gly  Ser  Arg  Lys  Leu  Ser  Cys  Ala  Ala  Ser  Gly  Phe  Thr
```

|  |  |  |  |  |  |  |  |  |  |  |  |  |  |  |  |
|---|---|---|---|---|---|---|---|---|---|---|---|---|---|---|---|
|  | | 20 | | | | | 25 | | | | | 30 | | | |
| TTC | AGT | AGC | TTT | GGA | ATG | CAC | TGG | CTT | CGT | CAG | GCT | CCA | GAG | AAG | GGG | 144
| Phe | Ser | Ser | Phe | Gly | Met | His | Trp | Val | Arg | Gln | Ala | Pro | Glu | Lys | Gly |
|  |  | 35 |  |  |  |  | 40 |  |  |  |  | 45 |  |  |  |
| CTG | GAG | TGG | GTC | GCA | TAT | ATT | AGT | AGT | GGC | AGT | AGT | ACT | ATC | TAC | TAT | 192
| Leu | Glu | Trp | Val | Ala | Tyr | Ile | Ser | Ser | Gly | Ser | Ser | Thr | Ile | Tyr | Tyr |
|  | 50 | | | | | 55 | | | | | 60 | | | | |
| GCA | GAC | ACA | GTG | AAG | GGC | CGA | TTC | ACC | ATC | TCC | AGA | GAC | AAT | CCC | AAG | 240
| Ala | Asp | Thr | Val | Lys | Gly | Arg | Phe | Thr | Ile | Ser | Arg | Asp | Asn | Pro | Lys |
| 65 | | | | | 70 | | | | | 75 | | | | | 80 |
| AAC | ACC | CTG | TTC | CTG | CAG | ATG | ACC | AGT | CTA | AGG | TCT | GAG | GAC | ACG | GCC | 288
| Asn | Thr | Leu | Phe | Leu | Gln | Met | Thr | Ser | Leu | Arg | Ser | Glu | Asp | Thr | Ala |
|  |  |  |  | 85 | | | | | 90 | | | | | 95 | |
| ATG | TAT | TAC | TGT | GCA | AGA | GAT | TAC | GGG | GCT | TAT | TGG | GGC | CAA | GGG | ACC | 336
| Met | Tyr | Tyr | Cys | Ala | Arg | Asp | Tyr | Gly | Ala | Tyr | Trp | Gly | Gln | Gly | Thr |
|  |  |  | 100 | | | | | 105 | | | | | 110 | | |
| CTG | GTC | ACC | GTC | TCC | TCA | GGT | GGA | GGC | GGT | TCA | GGC | GGA | GGT | GGC | TCT | 384
| Leu | Val | Thr | Val | Ser | Ser | Gly | Gly | Gly | Gly | Ser | Gly | Gly | Gly | Gly | Ser |
|  |  | 115 | | | | | 120 | | | | | 125 | | | |
| GGC | GGT | GGC | GGA | TCC | CAA | ATT | GTT | CTC | ACC | CAG | TCT | CCA | GCA | ATC | ATG | 432
| Gly | Gly | Gly | Gly | Ser | Gln | Ile | Val | Leu | Thr | Gln | Ser | Pro | Ala | Ile | Met |
| 130 | | | | | 135 | | | | | 140 | | | | | |
| TCT | GCA | TCT | CCA | GGG | GAG | AAA | GTC | ACC | ATG | ACC | TGC | AGT | GCC | AGT | TCA | 480
| Ser | Ala | Ser | Pro | Gly | Glu | Lys | Val | Thr | Met | Thr | Cys | Ser | Ala | Ser | Ser |
| 145 | | | | | 150 | | | | | 155 | | | | | 160 |
| AGT | GTA | AGG | TAC | ATG | AAC | TGG | TTC | CAA | CAG | AAG | TCA | GGC | ACC | TCC | CCC | 528
| Ser | Val | Arg | Tyr | Met | Asn | Trp | Phe | Gln | Gln | Lys | Ser | Gly | Thr | Ser | Pro |
|  |  |  |  | 165 | | | | | 170 | | | | | 175 | |
| AAG | CGC | TGG | ACA | TAT | GAC | ACA | TCC | AAA | CTG | TCT | TCT | GGA | GTC | CCT | GCT | 576
| Lys | Arg | Trp | Thr | Tyr | Asp | Thr | Ser | Lys | Leu | Ser | Ser | Gly | Val | Pro | Ala |
|  |  |  | 180 | | | | | 185 | | | | | 190 | | |
| CGC | TTC | AGT | GGC | AGT | GGG | TCT | GGG | ACC | TCT | TAC | TCT | CTC | ACA | ATC | AGC | 624
| Arg | Phe | Ser | Gly | Ser | Gly | Ser | Gly | Thr | Ser | Tyr | Ser | Leu | Thr | Ile | Ser |
|  |  | 195 | | | | | 200 | | | | | 205 | | | |
| AGC | ATG | GAG | GCT | GAA | GAT | GCT | GCC | ACT | TAT | TAC | TGC | CAG | CAG | TGG | AGT | 672
| Ser | Met | Glu | Ala | Glu | Asp | Ala | Ala | Thr | Tyr | Tyr | Cys | Gln | Gln | Trp | Ser |
| 210 | | | | | 215 | | | | | 220 | | | | | |
| AGT | AAT | CCA | CTC | ACT | TTC | GGT | GCT | GGG | ACC | AAG | CTT | GAA | CTG | AAA | CGG | 720
| Ser | Asn | Pro | Leu | Thr | Phe | Gly | Ala | Gly | Thr | Lys | Leu | Glu | Leu | Lys | Arg |
| 225 | | | | | 230 | | | | | 235 | | | | | 240 |
| TGATAATCTA | GAACCGCG | | | | | | | | | | | | | | | 738

( 2 ) INFORMATION FOR SEQ ID NO:25:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Gln | Arg | Val | Asp | Tyr | Val | Gln | Leu | Val | Glu | Leu | Gly | Gly | Gly | Phe | Val |
|---|---|---|---|---|---|---|---|---|---|---|---|---|---|---|---|
| 1 | | | | 5 | | | | | 10 | | | | | 15 | |
| Gln | Pro | Gly | Gly | Ser | Arg | Lys | Leu | Ser | Cys | Ala | Ala | Ser | Gly | Phe | Thr |
| | | | 20 | | | | | 25 | | | | | 30 | | |
| Phe | Ser | Ser | Phe | Gly | Met | His | Trp | Val | Arg | Gln | Ala | Pro | Glu | Lys | Gly |
| | | 35 | | | | | 40 | | | | | 45 | | | |
| Leu | Glu | Trp | Val | Ala | Tyr | Ile | Ser | Ser | Gly | Ser | Ser | Thr | Ile | Tyr | Tyr |
| | 50 | | | | | 55 | | | | | 60 | | | | |

| Ala | Asp | Thr | Val | Lys | Gly | Arg | Phe | Thr | Ile | Ser | Arg | Asp | Asn | Pro | Lys |
| 65 | | | | 70 | | | | | 75 | | | | | | 80 |

| Asn | Thr | Leu | Phe | Leu | Gln | Met | Thr | Ser | Leu | Arg | Ser | Glu | Asp | Thr | Ala |
| | | | | 85 | | | | | 90 | | | | | 95 | |

| Met | Tyr | Tyr | Cys | Ala | Arg | Asp | Tyr | Gly | Ala | Tyr | Trp | Gly | Gln | Gly | Thr |
| | | | 100 | | | | | 105 | | | | | | 110 | |

| Leu | Val | Thr | Val | Ser | Ser | Gly | Gly | Gly | Gly | Ser | Gly | Gly | Gly | Gly | Ser |
| | | 115 | | | | | 120 | | | | | 125 | | | |

| Gly | Gly | Gly | Gly | Ser | Gln | Ile | Val | Leu | Thr | Gln | Ser | Pro | Ala | Ile | Met |
| | 130 | | | | | 135 | | | | | 140 | | | | |

| Ser | Ala | Ser | Pro | Gly | Glu | Lys | Val | Thr | Met | Thr | Cys | Ser | Ala | Ser | Ser |
| 145 | | | | | 150 | | | | | 155 | | | | | 160 |

| Ser | Val | Arg | Tyr | Met | Asn | Trp | Phe | Gln | Gln | Lys | Ser | Gly | Thr | Ser | Pro |
| | | | | 165 | | | | | 170 | | | | | 175 | |

| Lys | Arg | Trp | Thr | Tyr | Asp | Thr | Ser | Lys | Leu | Ser | Ser | Gly | Val | Pro | Ala |
| | | | 180 | | | | | 185 | | | | | 190 | | |

| Arg | Phe | Ser | Gly | Ser | Gly | Ser | Gly | Thr | Ser | Tyr | Ser | Leu | Thr | Ile | Ser |
| | | 195 | | | | | 200 | | | | | 205 | | | |

| Ser | Met | Glu | Ala | Glu | Asp | Ala | Ala | Thr | Tyr | Tyr | Cys | Gln | Gln | Trp | Ser |
| | 210 | | | | | 215 | | | | | 220 | | | | |

| Ser | Asn | Pro | Leu | Thr | Phe | Gly | Ala | Gly | Thr | Lys | Leu | Glu | Leu | Lys | Arg |
| 225 | | | | | 230 | | | | | 235 | | | | | 240 |

( 2 ) INFORMATION FOR SEQ ID NO:26:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..54
        ( D ) OTHER INFORMATION: /note= "Molecule 1-54 encodes a
            peptide."

( i x ) FEATURE:
        ( A ) NAME/KEY: CDS
        ( B ) LOCATION: 91..180
        ( D ) OTHER INFORMATION: /note= "Molecule 91-180 encodes a
            peptide."

( x i ) SEQUENCE DESCRIPTION: SEQ ID NO:26:

| GCA | AGA | GAT | TAC | GGG | GCT | TAT | TGG | GGC | CAA | GGG | ACC | CTG | GTC | ACC | GTC | 48 |
| Ala | Arg | Asp | Tyr | Gly | Ala | Tyr | Trp | Gly | Gln | Gly | Thr | Leu | Val | Thr | Val | |
| 1 | | | | 5 | | | | | 10 | | | | | 15 | | |

| TCC | TCA | TGATAATGCG | AATTCTATTT | CAAGGAGACA | GTCATA | ATG | AAA | TAC | CTA | 102 |
| Ser | Ser | | | | | Met | Lys | Tyr | Leu | |
| | | | | | | 1 | | | | |

| TTG | CCT | ACG | GCA | GCC | GCT | GGA | TTG | TTA | TTA | CTC | GCT | GCC | CAA | CCA | GCC | 150 |
| Leu | Pro | Thr | Ala | Ala | Ala | Gly | Leu | Leu | Leu | Leu | Ala | Ala | Gln | Pro | Ala | |
| 5 | | | | | 10 | | | | | 15 | | | | | 20 | |

| ATG | GCC | CAA | ATT | GTT | CTC | ACC | CAG | TCT | CCA | 180 |
| Met | Ala | Gln | Ile | Val | Leu | Thr | Gln | Ser | Pro | |
| | | | | 25 | | | | | 30 | |

( 2 ) INFORMATION FOR SEQ ID NO:27:

( i ) SEQUENCE CHARACTERISTICS:
        ( A ) LENGTH: 18 amino acids
        ( B ) TYPE: amino acid 5,882,924

39

40

-continued ( D ) TOPOLOGY: linear ( i i ) MOLECULE TYPE: protein ( x i ) SEQUENCE DESCRIPTION: SEQ ID NO:27:

Ala  Arg  Asp  Tyr  Gly  Ala  Tyr  Trp  Gly  Gln  Gly  Thr  Leu  Val  Thr  Val
 1              5                        10                       15

Ser  Ser ( 2 ) INFORMATION FOR SEQ ID NO:28:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Met  Lys  Tyr  Leu  Leu  Pro  Thr  Ala  Ala  Ala  Gly  Leu  Leu  Leu  Leu  Ala
 1              5                        10                       15

Ala  Gln  Pro  Ala  Met  Ala  Gln  Ile  Val  Leu  Thr  Gln  Ser  Pro
                20                       25                       30

( 2 ) INFORMATION FOR SEQ ID NO:29:

( i ) SEQUENCE CHARACTERISTICS:
        ( A ) LENGTH: 793 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 16..354
        ( D ) OTHER INFORMATION: /note= "Molecules 16-354 encode a
              peptide."

( i x ) FEATURE:
        ( A ) NAME/KEY: CDS
        ( B ) LOCATION: 383..775
        ( D ) OTHER INFORMATION: /note= "Molecules 383-775 encode a
              peptide."

( x i ) SEQUENCE DESCRIPTION: SEQ ID NO:29:

CAGCGAGTCG  ACTAC  GTA  CAG  CTG  GTG  GAG  CTT  GGG  GGA  GGC  TTT  GTG  CAG        51
                  Val  Gln  Leu  Val  Glu  Leu  Gly  Gly  Gly  Phe  Val  Gln
                   1              5                        10

CCT  GGA  GGG  TCC  CGG  AAA  CTC  TCC  TGT  GCA  GCC  TCT  GGA  TTC  ACT  TTC        99
Pro  Gly  Gly  Ser  Arg  Lys  Leu  Ser  Cys  Ala  Ala  Ser  Gly  Phe  Thr  Phe
               15                       20                       25

AGT  AGC  TTT  GGA  ATG  CAC  TGG  GTT  CGT  CAG  GCT  CCA  GAG  AAG  GGG  CTG       147
Ser  Ser  Phe  Gly  Met  His  Trp  Val  Arg  Gln  Ala  Pro  Glu  Lys  Gly  Leu
      30                       35                       40

GAG  TGG  GTC  GCA  TAT  ATT  AGT  AGT  GGC  AGT  AGT  ACT  ATC  TAC  TAT  GCA       195
Glu  Trp  Val  Ala  Tyr  Ile  Ser  Ser  Gly  Ser  Ser  Thr  Ile  Tyr  Tyr  Ala
 45                        50                       55                       60

GAC  ACA  GTG  AAG  GGC  CGA  TTC  ACC  ATC  TCC  AGA  GAC  AAT  CCC  AAG  AAC       243
Asp  Thr  Val  Lys  Gly  Arg  Phe  Thr  Ile  Ser  Arg  Asp  Asn  Pro  Lys  Asn
                    65                       70                       75

ACC  CTG  TTC  CTG  CAG  ATG  ACC  AGT  CTA  AGG  TCT  GAG  GAC  ACG  GCC  ATG       291
Thr  Leu  Phe  Leu  Gln  Met  Thr  Ser  Leu  Arg  Ser  Glu  Asp  Thr  Ala  Met
               80                       85                       90

TAT  TAC  TGT  GCA  AGA  GAT  TAC  GGG  GCT  TAT  TGG  GGC  CAA  GGG  ACC  CTG       339
Tyr  Tyr  Cys  Ala  Arg  Asp  Tyr  Gly  Ala  Tyr  Trp  Gly  Gln  Gly  Thr  Leu

```
              95                      100                       105
GTC  ACC  GTC  TCC  TCA  TGATAATGCG  AATTCATTTG  TACATGGA  GAA  AAT  AAA     391
Val  Thr  Val  Ser  Ser                                    Glu  Asn  Lys
110

GTG  AAA  CAA  AGC  ACT  ATT  GCA  CTG  GCA  CTC  TTA  CCG  TTA  CTG  TTT  ACC    439
Val  Lys  Gln  Ser  Thr  Ile  Ala  Leu  Ala  Leu  Leu  Pro  Leu  Leu  Phe  Thr
       5                  10                       15

CCT  GTG  ACA  AAA  GCC  CAA  ATT  GTT  CTC  ACC  CAG  TCT  CCA  GCA  ATC  ATG    487
Pro  Val  Thr  Lys  Ala  Gln  Ile  Val  Leu  Thr  Gln  Ser  Pro  Ala  Ile  Met
 20                       25                       30                       35

TCT  GCA  TCT  CCA  GGG  GAG  AAA  GTC  ACC  ATG  ACC  TGC  AGT  GCC  AGT  TCA    535
Ser  Ala  Ser  Pro  Gly  Glu  Lys  Val  Thr  Met  Thr  Cys  Ser  Ala  Ser  Ser
                      40                       45                       50

AGT  GTA  AGG  TAC  ATG  AAC  TGG  TTC  CAA  CAG  AAG  TCA  GGC  ACC  TCC  CCC    583
Ser  Val  Arg  Tyr  Met  Asn  Trp  Phe  Gln  Gln  Lys  Ser  Gly  Thr  Ser  Pro
                55                       60                       65

AAG  CGC  TGG  ACA  TAT  GAC  ACA  TCC  AAA  CTG  TCT  TCT  GGA  GTC  CCT  GCT    631
Lys  Arg  Trp  Thr  Tyr  Asp  Thr  Ser  Lys  Leu  Ser  Ser  Gly  Val  Pro  Ala
           70                       75                       80

CGC  TTC  AGT  GGC  AGT  GGG  TCT  GGG  ACC  TCT  TAC  TCT  CTC  ACA  ATC  AGC    679
Arg  Phe  Ser  Gly  Ser  Gly  Ser  Gly  Thr  Ser  Tyr  Ser  Leu  Thr  Ile  Ser
      85                       90                       95

AGC  ATG  GAG  GCT  GAA  GAT  GCT  GCC  ACT  TAT  TAC  TGC  CAG  CAG  TGG  AGT    727
Ser  Met  Glu  Ala  Glu  Asp  Ala  Ala  Thr  Tyr  Tyr  Cys  Gln  Gln  Trp  Ser
100                      105                      110                      115

AGT  AAT  CCA  CTC  ACT  TTC  GGT  GCT  GGG  ACC  AAG  CTT  GAA  CTG  AAA  CGG    775
Ser  Asn  Pro  Leu  Thr  Phe  Gly  Ala  Gly  Thr  Lys  Leu  Glu  Leu  Lys  Arg
                     120                      125                      130

TGATAATCTA  GAACCGCG                                                              793
```

( 2 ) INFORMATION FOR SEQ ID NO:30:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Val  Gln  Leu  Val  Glu  Leu  Gly  Gly  Gly  Phe  Val  Gln  Pro  Gly  Gly  Ser
 1                    5                      10                       15

Arg  Lys  Leu  Ser  Cys  Ala  Ala  Ser  Gly  Phe  Thr  Phe  Ser  Ser  Phe  Gly
              20                       25                       30

Met  His  Trp  Val  Arg  Gln  Ala  Pro  Glu  Lys  Gly  Leu  Glu  Trp  Val  Ala
           35                       40                       45

Tyr  Ile  Ser  Ser  Gly  Ser  Ser  Thr  Ile  Tyr  Tyr  Ala  Asp  Thr  Val  Lys
      50                       55                       60

Gly  Arg  Phe  Thr  Ile  Ser  Arg  Asp  Asn  Pro  Lys  Asn  Thr  Leu  Phe  Leu
 65                       70                       75                       80

Gln  Met  Thr  Ser  Leu  Arg  Ser  Glu  Asp  Thr  Ala  Met  Tyr  Tyr  Cys  Ala
                 85                       90                       95

Arg  Asp  Tyr  Gly  Ala  Tyr  Trp  Gly  Gln  Gly  Thr  Leu  Val  Thr  Val  Ser
               100                      105                      110

Ser
```

( 2 ) INFORMATION FOR SEQ ID NO:31:

( i ) SEQUENCE CHARACTERISTICS:
        ( A ) LENGTH: 128 amino acids (B) TYPE: amino acid
(D) TOPOLOGY: linear (i i) MOLECULE TYPE: protein (x i) SEQUENCE DESCRIPTION: SEQ ID NO:31:

| Val | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Gln | Ile | Val | Leu | Thr | Gln | Ser | Pro | Ala | Ile | Met |
|---|---|---|---|---|---|---|---|---|---|---|---|---|---|---|---|
| | | | 20 | | | | | 25 | | | | | 30 | | |

| Ser | Ala | Ser | Pro | Gly | Glu | Lys | Val | Thr | Met | Thr | Cys | Ser | Ala | Ser | Ser |
|---|---|---|---|---|---|---|---|---|---|---|---|---|---|---|---|
| | | 35 | | | | | 40 | | | | | 45 | | | |

| Ser | Val | Arg | Tyr | Met | Asn | Trp | Phe | Gln | Gln | Lys | Ser | Gly | Thr | Ser | Pro |
|---|---|---|---|---|---|---|---|---|---|---|---|---|---|---|---|
| | 50 | | | | | 55 | | | | | 60 | | | | |

| Lys | Arg | Trp | Thr | Tyr | Asp | Thr | Ser | Lys | Leu | Ser | Ser | Gly | Val | Pro | Ala |
|---|---|---|---|---|---|---|---|---|---|---|---|---|---|---|---|
| 65 | | | | | 70 | | | | | 75 | | | | | 80 |

| Arg | Phe | Ser | Gly | Ser | Gly | Ser | Gly | Thr | Ser | Tyr | Ser | Leu | Thr | Ile | Ser |
|---|---|---|---|---|---|---|---|---|---|---|---|---|---|---|---|
| | | | | 85 | | | | | 90 | | | | | 95 | |

| Ser | Met | Glu | Ala | Glu | Asp | Ala | Ala | Thr | Tyr | Tyr | Cys | Gln | Gln | Trp | Ser |
|---|---|---|---|---|---|---|---|---|---|---|---|---|---|---|---|
| | | | 100 | | | | | 105 | | | | | 110 | | |

| Ser | Asn | Pro | Leu | Thr | Phe | Gly | Ala | Gly | Thr | Lys | Leu | Glu | Leu | Lys | Arg |
|---|---|---|---|---|---|---|---|---|---|---|---|---|---|---|---|
| | | 115 | | | | | 120 | | | | | 125 | | | |

(2) INFORMATION FOR SEQ ID NO:32:

(i) SEQUENCE CHARACTERISTICS:
      (A) LENGTH: 784 base pairs
      (B) TYPE: nucleic acid
      (C) STRANDEDNESS: double
      (D) TOPOLOGY: linear (i i) MOLECULE TYPE: DNA (genomic)

(i x) FEATURE:
      (A) NAME/KEY: CDS
      (B) LOCATION: 13..330
      (D) OTHER INFORMATION: /note= "Molecules 13-330 encode a peptide."

(i x) FEATURE:
      (A) NAME/KEY: CDS
      (B) LOCATION: 365..769
      (D) OTHER INFORMATION: /note= "Molecules 365-769 encode a peptide."

(x i) SEQUENCE DESCRIPTION: SEQ ID NO:32:

| ACAGTCGACG | AT | ATC | GTT | CTC | ACC | CAG | TCT | CCA | GCA | ATC | ATG | TCT | GCA | 48 |
|---|---|---|---|---|---|---|---|---|---|---|---|---|---|---|
| | | Ile | Val | Leu | Thr | Gln | Ser | Pro | Ala | Ile | Met | Ser | Ala | |
| | | 1 | | | | 5 | | | | | 10 | | | |

| TCT | CCA | GGG | GAG | AAA | GTC | ACC | ATG | ACC | TGC | AGT | GCC | AGT | TCA | AGT | GTA | 96 |
|---|---|---|---|---|---|---|---|---|---|---|---|---|---|---|---|---|
| Ser | Pro | Gly | Glu | Lys | Val | Thr | Met | Thr | Cys | Ser | Ala | Ser | Ser | Ser | Val | |
| | | 15 | | | | | 20 | | | | | 25 | | | | |

| AGG | TAC | ATG | AAC | TGG | TTC | CAA | CAG | AAG | TCA | GGC | ACC | TCC | CCC | AAG | CGC | 144 |
|---|---|---|---|---|---|---|---|---|---|---|---|---|---|---|---|---|
| Arg | Tyr | Met | Asn | Trp | Phe | Gln | Gln | Lys | Ser | Gly | Thr | Ser | Pro | Lys | Arg | |
| | | 30 | | | | | 35 | | | | | 40 | | | | |

| TGG | ACA | TAT | GAC | ACA | TCC | AAA | CTG | TCT | TCT | GGA | GTC | CCT | GCT | CGC | TTC | 192 |
|---|---|---|---|---|---|---|---|---|---|---|---|---|---|---|---|---|
| Trp | Thr | Tyr | Asp | Thr | Ser | Lys | Leu | Ser | Ser | Gly | Val | Pro | Ala | Arg | Phe | |
| 45 | | | | | 50 | | | | | 55 | | | | | 60 | |

| AGT | GGC | AGT | GGG | TCT | GGG | ACC | TCT | TAC | TCT | CTC | ACA | ATC | AGC | AGC | ATG | 240 |
|---|---|---|---|---|---|---|---|---|---|---|---|---|---|---|---|---|
| Ser | Gly | Ser | Gly | Ser | Gly | Thr | Ser | Tyr | Ser | Leu | Thr | Ile | Ser | Ser | Met | |
| | | | | 65 | | | | | 70 | | | | | 75 | | |

| GAG | GCT | GAA | GAT | GCT | GCC | ACT | TAT | TAC | TGC | CAG | CAG | TGG | AGT | AGT | AAT | 288 |
|---|---|---|---|---|---|---|---|---|---|---|---|---|---|---|---|---|
| Glu | Ala | Glu | Asp | Ala | Ala | Thr | Tyr | Tyr | Cys | Gln | Gln | Trp | Ser | Ser | Asn | |
| | | | 80 | | | | | 85 | | | | | 90 | | | |

```
CCA CTC ACT TTC GGT GCT GGG ACC AAG CTT GAA CTG AAA CGG                     330
Pro Leu Thr Phe Gly Ala Gly Thr Lys Leu Glu Leu Lys Arg
        95                      100                 105

TGATAAGAAT TCATTTGTAC ATGGAGAAAA TAAA GTG AAA CAA AGC ACT ATT               382
                                     Val Lys Gln Ser Thr Ile
                                      1               5

GCA CTG GCA CTC TTA CCG TTA CTG TTT ACC CCT GTG ACA AAA GCC GAT             430
Ala Leu Ala Leu Leu Pro Leu Leu Phe Thr Pro Val Thr Lys Ala Asp
            10              15                  20

GTA CAG CTG GTG GAG CTT GGG GGA GGC TTT GTG CAG CCT GGA GGG TCC             478
Val Gln Leu Val Glu Leu Gly Gly Gly Phe Val Gln Pro Gly Gly Ser
        25              30                  35

CGG AAA CTC TCC TGT GCA GCC TCT GGA TTC ACT TTC AGT AGC TTT GGA             526
Arg Lys Leu Ser Cys Ala Ala Ser Gly Phe Thr Phe Ser Ser Phe Gly
    40              45                  50

ATG CAC TGG GTT CGT CAG GCT CCA GAG AAG GGG CTG GAG TGG GTC GCA             574
Met His Trp Val Arg Gln Ala Pro Glu Lys Gly Leu Glu Trp Val Ala
 55              60                  65                      70

TAT ATT AGT AGT GGC AGT AGT ACT ATC TAC TAT GCA GAC ACA GTG AAG             622
Tyr Ile Ser Ser Gly Ser Ser Thr Ile Tyr Tyr Ala Asp Thr Val Lys
                75                  80                  85

GGC CGA TTC ACC ATC TCC AGA GAC AAT CCC AAG AAC ACC CTG TTC CTG             670
Gly Arg Phe Thr Ile Ser Arg Asp Asn Pro Lys Asn Thr Leu Phe Leu
            90                  95                  100

CAG ATG ACC AGT CTA AGG TCT GAG GAC ACG GCC ATG TAT TAC TGT GCA             718
Gln Met Thr Ser Leu Arg Ser Glu Asp Thr Ala Met Tyr Tyr Cys Ala
        105                 110                 115

AGA GAT TAC GGG GCT TAT TGG GGC CAA GGG ACC CTG GTC ACC GTC TCC             766
Arg Asp Tyr Gly Ala Tyr Trp Gly Gln Gly Thr Leu Val Thr Val Ser
    120                 125                 130

TCA TGATAATCTA GATTC                                                        784
Ser
135
```

(2) INFORMATION FOR SEQ ID NO:33:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:33:

```
Ile Val Leu Thr Gln Ser Pro Ala Ile Met Ser Ala Ser Pro Gly Glu
 1               5                  10                  15

Lys Val Thr Met Thr Cys Ser Ala Ser Ser Val Arg Tyr Met Asn
            20                  25                  30

Trp Phe Gln Gln Lys Ser Gly Thr Ser Pro Lys Arg Trp Thr Tyr Asp
        35                  40                  45

Thr Ser Lys Leu Ser Ser Gly Val Pro Ala Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Leu Thr Phe
                85                  90                  95

Gly Ala Gly Thr Lys Leu Glu Leu Lys Arg
            100                 105
```

(2) INFORMATION FOR SEQ ID NO:34:

( i ) SEQUENCE CHARACTERISTICS:
    ( A ) LENGTH: 135 amino acids
    ( B ) TYPE: amino acid
    ( D ) TOPOLOGY: linear ( i i ) MOLECULE TYPE: protein ( x i ) SEQUENCE DESCRIPTION: SEQ ID NO:34:

```
Val Lys Gln Ser Thr Ile Ala Leu Ala Leu Leu Pro Leu Leu Phe Thr
 1               5                  10                  15
Pro Val Thr Lys Ala Asp Val Gln Leu Val Glu Leu Gly Gly Gly Phe
             20                  25                  30
Val Gln Pro Gly Gly Ser Arg Lys Leu Ser Cys Ala Ala Ser Gly Phe
         35                  40                  45
Thr Phe Ser Ser Phe Gly Met His Trp Val Arg Gln Ala Pro Glu Lys
     50                  55                  60
Gly Leu Glu Trp Val Ala Tyr Ile Ser Ser Gly Ser Ser Thr Ile Tyr
 65                  70                  75                  80
Tyr Ala Asp Thr Val Lys Gly Arg Phe Thr Ile Ser Arg Asp Asn Pro
                 85                  90                  95
Lys Asn Thr Leu Phe Leu Gln Met Thr Ser Leu Arg Ser Glu Asp Thr
             100                 105                 110
Ala Met Tyr Tyr Cys Ala Arg Asp Tyr Gly Ala Tyr Trp Gly Gln Gly
         115                 120                 125
Thr Leu Val Thr Val Ser Ser
     130                 135
```

( 2 ) INFORMATION FOR SEQ ID NO:35:

( i ) SEQUENCE CHARACTERISTICS:
        ( A ) LENGTH: 959 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 264..959
        ( D ) OTHER INFORMATION: /note= "Molecule 264-959 encode a
            peptide."

( x i ) SEQUENCE DESCRIPTION: SEQ ID NO:35:

```
ACGCGTTTCT TTATTAGTGG TTGCAGTCTC GCTCATAATC GCTCCGTTTA CTTCTGTTTC         60

AAACAATTGA TCCATTGAGA CTCAATGGAA TTACCTTGAT GTGCAAGTGA GATATGGACA        120

AAAAATGTAA ATTCAAGGTC AAAACTCATA AAAACACTGT TTTTGATCG AGATTGGATT         180

ATTCTAAGTC TGCATTTTTA TCAAAGAAGA TAAAAAAACC AGTAAAGTCT GAGTGTTGGG        240

ACAGGGAGAT ACTGGGACAT TAG ATG TTC GGA TTA GGA CAC AAC TCA AAA            290
                         Met Phe Gly Leu Gly His Asn Ser Lys
                          1                   5

GAG ATA TCG ATG AGT CAT ATT GGT ACT AAA TTC ATT CTT GCT GAA AAA          338
Glu Ile Ser Met Ser His Ile Gly Thr Lys Phe Ile Leu Ala Glu Lys
 10              15                  20                  25

TTT ACC TTC GAT CCC CTA AGC AAT ACT CTG ATT GAC AAA GAA GAT AGT          386
Phe Thr Phe Asp Pro Leu Ser Asn Thr Leu Ile Asp Lys Gly Asp Ser
                 30                  35                  40

GAA GAG ATC ATT CGA TTA GGC AGC AAC GAA AGC CGA ATT CTT TGG CTG          434
Glu Glu Ile Ile Arg Leu Gly Ser Asn Glu Ser Arg Ile Leu Trp Leu
             45                  50                  55

CTG GCC CAA CGT CCA AAC GAG GTG ATT TCT CGC AAT GAT TTG CAT GAC          482
```

```
Leu  Ala  Gln  Arg  Pro  Asn  Glu  Val  Ile  Ser  Arg  Asn  Asp  Leu  His  Asp
          60                  65                  70

TTT  GTT  TGG  CGA  GAG  CAA  GGT  TTT  GAA  GTC  GAT  GAT  TCC  AGC  TTA  ACC      530
Phe  Val  Trp  Arg  Glu  Gln  Gly  Phe  Glu  Val  Asp  Asp  Ser  Ser  Leu  Thr
     75                  80                  85

CAA  GCC  ATT  TCG  ACT  CTG  CGC  AAA  ATG  CTC  AAA  GAT  TCG  ACA  AAG  TCC      578
Gln  Ala  Ile  Ser  Thr  Leu  Arg  Lys  Met  Leu  Lys  Asp  Ser  Thr  Lys  Ser
90                       95                  100                           105

CCA  CAA  TAC  GTC  AAA  ACG  GTT  CCG  AAG  CGC  GGT  TAC  CAA  TTG  ATC  GCC      626
Pro  Gln  Tyr  Val  Lys  Thr  Val  Pro  Lys  Arg  Gly  Tyr  Gln  Leu  Ile  Ala
               110                      115                      120

CGA  GTG  GAA  ACG  GTT  GAA  GAA  GAG  ATG  GCT  CGC  GAA  AAC  GAA  GCT  GCT      674
Arg  Val  Glu  Thr  Val  Glu  Glu  Glu  Met  Ala  Arg  Glu  Asn  Glu  Ala  Ala
          125                      130                      135

CAT  GAC  ATC  TCT  CAG  CCA  GAA  TCT  GTC  AAT  GAA  TAC  GCA  GAA  TCA  AGC      722
His  Asp  Ile  Ser  Gln  Pro  Glu  Ser  Val  Asn  Glu  Tyr  Ala  Glu  Ser  Ser
     140                      145                      150

AGT  GTG  CCT  TCA  TCA  GCC  ACT  GTA  GTG  AAC  ACA  CCG  CAG  CCA  GCC  AAT      770
Ser  Val  Pro  Ser  Ser  Ala  Thr  Val  Val  Asn  Thr  Pro  Gln  Pro  Ala  Asn
155                      160                      165                      170

GTC  GTG  GCG  AAT  AAA  TCG  GCT  CCA  AAC  TTG  GGG  AAT  CGA  CTG  TTT  ATT      818
Val  Val  Ala  Asn  Lys  Ser  Ala  Pro  Asn  Leu  Gly  Asn  Arg  Leu  Phe  Ile
               175                      180                      185

CTG  ATA  GCG  GTC  TTA  CTT  CCC  CTC  GCA  GTA  TTA  CTG  CTC  ACT  AAC  CCA      866
Leu  Ile  Ala  Val  Leu  Leu  Pro  Leu  Ala  Val  Leu  Leu  Leu  Thr  Asn  Pro
          190                      195                      200

AGC  CAA  TCC  AGC  TTT  AAA  CCC  CTA  ACG  CCT  GTT  CTG  GAA  AAC  CGG  GCT      914
Ser  Gln  Ser  Ser  Phe  Lys  Pro  Leu  Thr  Pro  Val  Leu  Glu  Asn  Arg  Ala
               205                      210                      215

GCT  CAG  GGC  GAT  ATT  ACT  GCA  CCC  GGC  GGT  GCT  CGC  CGT  TTA  ACG           959
Ala  Gln  Gly  Asp  Ile  Thr  Ala  Pro  Gly  Gly  Ala  Arg  Arg  Leu  Thr
     220                      225                      230
```

( 2 ) INFORMATION FOR SEQ ID NO:36:

( i ) SEQUENCE CHARACTERISTICS:
     ( A ) LENGTH: 232 amino acids
     ( B ) TYPE: amino acid
     ( D ) TOPOLOGY: linear ( i i ) MOLECULE TYPE: protein ( x i ) SEQUENCE DESCRIPTION: SEQ ID NO:36:

```
Met  Phe  Gly  Leu  Gly  His  Asn  Ser  Lys  Glu  Ile  Ser  Met  Ser  His  Ile
  1                 5                  10                           15

Gly  Thr  Lys  Phe  Ile  Leu  Ala  Glu  Lys  Phe  Thr  Phe  Asp  Pro  Leu  Ser
               20                  25                       30

Asn  Thr  Leu  Ile  Asp  Lys  Glu  Asp  Ser  Glu  Glu  Ile  Ile  Arg  Leu  Gly
          35                  40                       45

Ser  Asn  Glu  Ser  Arg  Ile  Leu  Trp  Leu  Leu  Ala  Gln  Arg  Pro  Asn  Glu
     50                       55                  60

Val  Ile  Ser  Arg  Asn  Asp  Leu  His  Asp  Phe  Val  Trp  Arg  Glu  Gln  Gly
65                       70                  75                            80

Phe  Glu  Val  Asp  Asp  Ser  Ser  Leu  Thr  Gln  Ala  Ile  Ser  Thr  Leu  Arg
                    85                  90                       95

Lys  Met  Leu  Lys  Asp  Ser  Thr  Lys  Ser  Pro  Gln  Tyr  Val  Lys  Thr  Val
               100                      105                      110

Pro  Lys  Arg  Gly  Tyr  Gln  Leu  Ile  Ala  Arg  Val  Glu  Thr  Val  Glu  Glu
          115                      120                      125

Glu  Met  Ala  Arg  Glu  Asn  Glu  Ala  Ala  His  Asp  Ile  Ser  Gln  Pro  Glu
```

|     |     |     |     | 130 |     |     |     |     | 135 |     |     |     |     | 140 |
| --- | --- | --- | --- | --- | --- | --- | --- | --- | --- | --- | --- | --- | --- | --- |

Ser Val Asn Glu Tyr Ala Glu Ser Ser Ser Val Pro Ser Ser Ala Thr
145                 150                 155                 160

Val Val Asn Thr Pro Gln Pro Ala Asn Val Val Ala Asn Lys Ser Ala
            165             170             175

Pro Asn Leu Gly Asn Arg Leu Phe Ile Leu Ile Ala Val Leu Leu Pro
        180             185             190

Leu Ala Val Leu Leu Leu Thr Asn Pro Ser Gln Ser Ser Phe Lys Pro
        195             200             205

Leu Thr Pro Val Leu Glu Asn Arg Ala Ala Gln Gly Asp Ile Thr Ala
        210             215             220

Pro Gly Gly Ala Arg Arg Leu Thr
225             230

( 2 ) INFORMATION FOR SEQ ID NO:37:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

CACGACGTTG TAGTACTACC TTTACCATAT A                      31

( 2 ) INFORMATION FOR SEQ ID NO:38:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

TTGGCTTGGG TTGATCAGGA TCCCAAGCTA GCTCGATTCC CCAAG          45

( 2 ) INFORMATION FOR SEQ ID NO:39:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

TCGAGCTAGC CCGGTTACCT TCATCATCGC TACCGTTGAA GGAGTACTGC     50

( 2 ) INFORMATION FOR SEQ ID NO:40:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

ATCAGGATCC CAACCACGAC AACCAGGATC AGGAACAGCA GTACTCCAAC AACGGTAGC    59

( 2 ) INFORMATION FOR SEQ ID NO:41:

( i ) SEQUENCE CHARACTERISTICS:
        ( A ) LENGTH: 738 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:41:

| | | | | | |
|---|---|---|---|---|---|
| GTCGCTCAGC | TGATGCATGT | CGACCACCTC | GAACCCCTC | CGAAACACGT | CGGACCTCCC | 60 |
| AGGGCCTTTG | AGAGGACACG | TCGGAGACCT | AAGTGAAAGT | CATCGAAACC | TTACGTGACC | 120 |
| CAAGCAGTCC | GAGGTCTCTT | CCCCGACCTC | ACCCAGCGTA | TATAATCATC | ACCGTCATCA | 180 |
| TGATAGATGA | TACGTCTGTG | TCACTTCCCG | GCTAAGTGGT | AGAGGTCTCT | GTTAGGGTTC | 240 |
| TTGTGGGACA | AGGACGTCTA | CTGGTCAGAT | TCCAGACTCC | TGTGCCGGTA | CATAATGACA | 300 |
| CGTTCTCTAA | TGCCCCGAAT | AACCCCGGTT | CCCTGGGACC | AGTGGCAGAG | GAGTCCACCT | 360 |
| CCGCCAAGTC | CGCCTCCACC | GAGACCGCCA | CCGCCTAGGG | TTTAACAAGA | GTGGGTCAGA | 420 |
| GGTCGTTAGT | ACAGACGTAG | AGGTCCCCTC | TTTCAGTGGT | ACTGGACGTC | ACGGTCAAGT | 480 |
| TCACATTCCA | TGTACTTGAC | CAAGGTTGTC | TTCAGTCCGT | GGAGGGGTT | CGCGACCTGT | 540 |
| ATACTGTGTA | GGTTTGACAG | AAGACCTCAG | GGACGAGCGA | AGTCACCGTC | ACCCAGACCC | 600 |
| TGGAGAATGA | GAGAGTGTTA | GTCGTCGTAC | CTCCGACTTC | TACGACGGTG | AATAATGACG | 660 |
| GTCGTCACCT | CATCATTAGG | TGAGTGAAAG | CCACGACCCT | GGTTCGAACT | TGACTTTGCC | 720 |
| ACTATTAGAT | CTTGGCGC | | | | | 738 |

( 2 ) INFORMATION FOR SEQ ID NO:42:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:42:

| | | | | | |
|---|---|---|---|---|---|
| CGTTCTCTAA | TGCCCCGAAT | AACCCCGGTT | CCCTGGGACC | AGTGGCAGAG | GAGTACTATT | 60 |
| ACGCTTAAGA | TAAAGTTCCT | CTGTCAGTAT | TACTTTATGG | ATAACGGATG | CCGTCGGCGA | 120 |
| CCTAACAATA | ATGAGCGACG | GGTTGGTCGG | TACCGGGTTT | AACAAGAGTG | GGTCAGAGGT | 180 |

( 2 ) INFORMATION FOR SEQ ID NO:43:

( i ) SEQUENCE CHARACTERISTICS:
        ( A ) LENGTH: 793 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:43:

| | | | | | |
|---|---|---|---|---|---|
| GTCGCTCAGC | TGATGCATGT | CGACCACCTC | GAACCCCTC | CGAAACACGT | CGGACCTCCC | 60 |
| AGGGCCTTTG | AGAGGACACG | TCGGAGACCT | AAGTGAAAGT | CATCGAAACC | TTACGTGACC | 120 |
| CAAGCAGTCC | GAGGTCTCTT | CCCCGACCTC | ACCCAGCGTA | TATAATCATC | ACCGTCATCA | 180 |
| TGATAGATGA | TACGTCTGTG | TCACTTCCCG | GCTAAGTGGT | AGAGGTCTCT | GTTAGGGTTC | 240 |
| TTGTGGGACA | AGGACGTCTA | CTGGTCAGAT | TCCAGACTCC | TGTGCCGGTA | CATAATGACA | 300 |

| | | | | | | |
|---|---|---|---|---|---|---|
| CGTTCTCTAA | TGCCCCGAAT | AACCCCGGTT | CCCTGGGACC | AGTGGCAGAG | GAGTACTATT | 360 |
| ACGCTTAAGT | AAACATGTAC | CTCTTTTATT | TCACTTTGTT | TCGTGATAAC | GTGACCGTGA | 420 |
| GAATGGCAAT | GACAAATGGG | GACACTGTTT | TCGGGTTTAA | CAAGAGTGGG | TCAGAGGTCG | 480 |
| TTAGTACAGA | CGTAGAGGTC | CCCTCTTTCA | GTGGTACTGG | ACGTCACGGT | CAAGTTCACA | 540 |
| TTCCATGTAC | TTGACCAAGG | TTGTCTTCAG | TCCGTGGAGG | GGGTTCGCGA | CCTGTATACT | 600 |
| GTGTAGGTTT | GACAGAAGAC | CTCAGGGACG | AGCGAAGTCA | CCGTCACCCA | GACCCTGGAG | 660 |
| AATGAGAGAG | TGTTAGTCGT | CGTACCTCCG | ACTTCTACGA | CGGTGAATAA | TGACGGTCGT | 720 |
| CACCTCATCA | TTAGGTGAGT | GAAAGCCACG | ACCCTGGTTC | GAACTTGACT | TTGCCACTAT | 780 |
| TAGATCTTGG | CGC | | | | | 793 |

( 2 ) INFORMATION FOR SEQ ID NO:44:

( i ) SEQUENCE CHARACTERISTICS:
        ( A ) LENGTH: 784 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:44:

| | | | | | | |
|---|---|---|---|---|---|---|
| TGTCAGCTGC | TATAGCAAGA | GTGGGTCAGA | GGTCGTTAGT | ACAGACGTAG | AGGTCCCCTC | 60 |
| TTTCAGTGGT | ACTGGACGTC | ACGGTCAAGT | TCACATTCCA | TGTACTTGAC | CAAGGTTGTC | 120 |
| TTCAGTCCGT | GGAGGGGGTT | CGCGACCTGT | ATACTGTGTA | GGTTTGACAG | AAGACCTCAG | 180 |
| GGACGAGCGA | AGTCACCGTC | ACCCAGACCC | TGGAGAATGA | GAGAGTGTTA | GTCGTCGTAC | 240 |
| CTCCGACTTC | TACGACGGTG | AATAATGACG | GTCGTCACCT | CATCATTAGG | TGAGTGAAAG | 300 |
| CCACGACCCT | GGTTCGAACT | TGACTTTGCC | ACTATTCTTA | AGTAAACATG | TACCTCTTTT | 360 |
| ATTTCACTTT | GTTTCGTGAT | AACGTGACCG | TGAGAATGGC | AATGACAAAT | GGGGACACTG | 420 |
| TTTTCGGCTA | CATGTCGACC | ACCTCGAACC | CCCTCCGAAA | CACGTCGGAC | CTCCCAGGGC | 480 |
| CTTTGAGAGG | ACACGTCGGA | GACCTAAGTG | AAAGTCATCG | AAACCTTACG | TGACCCAAGC | 540 |
| AGTCCGAGGT | CTCTTCCCCG | ACCTCACCCA | GCGTATATAA | TCATCACCGT | CATCATGATA | 600 |
| GATGATACGT | CTGTGTCACT | TCCCGGCTAA | GTGGTAGAGG | TCTCTGTTAG | GGTTCTTGTG | 660 |
| GGACAAGGAC | GTCTACTGGT | CAGATTCCAG | ACTCCTGTGC | CGGTACATAA | TGACACGTTC | 720 |
| TCTAATGCCC | CGAATAACCC | CGGTTCCCTG | GGACCAGTGG | CAGAGGAGTA | CTATTAGATC | 780 |
| TAAG | | | | | | 784 |

( 2 ) INFORMATION FOR SEQ ID NO:45:

( i ) SEQUENCE CHARACTERISTICS:
        ( A ) LENGTH: 960 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:45:

| | | | | | | |
|---|---|---|---|---|---|---|
| TGCGCAAAGA | AATAATCACC | AACGTCAGAG | CGAGTATTAG | CGAGGCAAAT | GAAGACAAAG | 60 |
| TTTGTTAACT | AGGTAACTCT | GAGTTACCTT | AATGGAACTA | CACGTTCACT | CTATACCTGT | 120 |
| TTTTTACATT | TAAGTTCCAG | TTTTGAGTAT | TTTTGTGACA | AAAAACTAGC | TCTAACCTAA | 180 |
| TAAGATTCAG | ACGTAAAAAT | AGTTTCTTCT | ATTTTTTTGG | TCATTTCAGA | CTCACAACCC | 240 |

-continued

| | | | | | | |
|---|---|---|---|---|---|---|
| TGTCCCTCTA | TGACCCTGTA | ATCTACAAGC | CTAATCCTGT | GTTGAGTTTT | CTCTATAGCT | 300 |
| ACTCAGTATA | ACCATGATTT | AAGTAAGAAC | GACTTTTTAA | ATGGAAGCTA | GGGGATTCGT | 360 |
| TATGAGACTA | ACTGTTTCTT | CTATCACTTC | TCTAGTAAGC | TAATCCGTCG | TTGCTTTCGG | 420 |
| CTTAAGAAAC | CGACGACCGG | GTTGCAGGTT | TGCTCCACTA | AAGAGCGTTA | CTAAACGTAC | 480 |
| TGAAACAAAC | CGCTCTCGTT | CCAAAACTTC | AGCTACTAAG | GTCGAATTGG | GTTCGGTAAA | 540 |
| GCTGAGACGC | GTTTTACGAG | TTTCTAAGCT | GTTTCAGGGG | TGTTATGCAG | TTTTGCCAAG | 600 |
| GCTTCGCGCC | AATGGTTAAC | TAGCGGGCTC | ACCTTTGCCA | ACTTCTTCTC | TACCGAGCGC | 660 |
| CTTTTGCTTC | GACGAGTACT | GTAGAGAGTC | GGTCTTAGAC | AGTTACTTAT | GCGTCTTAGT | 720 |
| TCGTCACACG | GAAGTAGTCG | GTGACATCAC | TTGTGTGGCG | TCGGTCGGTT | ACAGCACCGC | 780 |
| TTATTTAGCC | GAGGTTTGAA | CCCCTTAGCT | GACAAATAAG | ACTATCGCCA | GAATGAAGGG | 840 |
| GAGCGTCATA | ATGACGAGTG | ATTGGGTTCG | GTTAGGTCGA | AATTTGGGGA | TTGCGGACAA | 900 |
| GACCTTTTGG | CCCGACGAGT | CCCGCTATAA | TGACGTGGGC | CGCCACGAGC | GGCAAATTGC | 960 |

VECTORS FOR THE GENETIC SELECTION OF LIGAND BINDING PROTEINS IN MICROORGANISMS BY MEANS OF SIGNAL TRANSDUCTION

CROSS REFERENCE TO RELATED APPLICATIONS

This application is a continuation of application Ser. No. 08/257,669, filed Jun. 8, 1994 now abandoned.

The invention relates to a process for genetically selecting proteins in microorganisms, to suitable micro-organisms and replicons for this process, and to processes for their preparation.

Previous attempts to obtain antibodies without immunization are based on the presentation of $F_{ab}$ fragments on coat proteins of the filamentous phage M13 or f1, and the enrichment of tightly. binding variants out of complex populations by adsorption to immobilized hapten, followed by desorption and biological multiplication of the phages which have been retained selectively on the hapten matrix. This biochemical/genetic enrichment method was popularized chiefly by R. Lerner and G. Winter.

In addition to this, it is known from Parsott and Mekalanos, J. Bakt., 173, 2842 (1991) that the product of the toxR gene of Vibrio cholerae ($M_r$=32527) is responsible for the coordinated expression of a plurality of virulence determinants, principally the cholera toxin itself (encoded in the ctxAB operon) and a series of other proteins. According to a model described by Miller et al. (Cell, 48, 271 (1987)), ToxR is a transmembrane protein possessing a carboxyterminal domain (AA202/294) which is located in the periplasm, a transmembrane helix and an aminoterminal domain (AA1–182) which is located in the cytoplasm, the said aminoterminal domain exhibiting homology to other bacterial transcription activators, such as OmpR, PhoM or PhoG. In performing this function, ToxR binds, as a membrane-anchored protein, directly to the promoter/operator region of the ctx operon and acts as a transcription activator. The operator sequence TTTGAT, which is repeated eight times and lies in the region between −50 and −112 (Tab. 1), is essential for the binding. Miller et al. were able to demonstrate that ToxR-mediated signal transduction can be represented in E. coli using an E. coli strain possessing a chromosomally integrated ctxlacZ gene fusion in which the gene for β-galactosidase (lacZ) is placed under the control of the ctx promoter. In this construction, the lacZ gene was placed in a continuous reading frame downstream of the first 28 codons of the ctxA gene. When the fusion gene comprising ToxR and phoA was transferred from a plasmid into the cells, it was possible to demonstrate transcription activation of the ctx promoter by way of β-galactosidase expression.

According to the model described by Miller, dimerization of the ToxR periplasmic domains represents the necessary and sufficient activation signal. This model was based on the finding that signal transduction was mediated (permanently "on" state) by a ToxR derivative in which the periplasmic domain had been removed and replaced by alkaline phosphatase, a dimeric protein which is located in the periplasm.

The object of the present invention now was to develop a selection process which makes possible the use of signal transduction for the direct genetic selection of proteins in bacterial populations and, at the same time, to extend the selection principle to other protein classes which, additionally, do not possess any properties which are of direct functional relevance in the microorganism employed.

In this context, it was found, surprisingly, that genetic selection of proteins which are capable of ligand binding is possible in microorganisms.

The present invention therefore relates to a process for the genetic selection in microorganisms of proteins which are capable of ligand binding, in which process a protein which is capable of ligand binding is presented extra-cytoplasmically and the signal of the ligand binding is passed on by signal transduction to the biosynthetic machinery of the microorganism for the purpose of expressing a detectable and/or selectable function.

For the purpose of the invention, extra-cytoplasmic denotes "on the outer surface of the inner membrane or the outer membrane of the microorganism", disposition of the protein on the outer surface of the inner membrane, i.e. in the periplasm, being preferred. In accordance with the invention, the activation signal can be triggered by interaction of an extracellular ligand with the protein, or by homodimerization or heterodimerization of the periplasmic protein. In this context, this dimerization can either take place directly between two proteins or be elicited with the aid of a suitable divalent hapten.

In the process according to the invention, the activation signal produced in this way is passed on to the biosynthetic machinery of the microorganism by means of a transmembrane helix and a cytoplasmically located regulatory domain, in particular a transcription activator or transcription repressor.

In the process according to the invention, a microorganism, which can suitably be used for genetic selection by transduction and which contains a genetically stable detectable and/or selectable function, is transformed with a replicon, in particular a plasmid, phage genome or phasmid, encoding a fusion protein comprising protein capable of ligand binding, transmembrane helix and regulatory domain, and the function generated by signal transduction is determined and/or selected for.

In a preferred embodiment of the invention, the detectable and selectable function is the expression of a gene which is under the control of a regulatable promoter and which encodes the detectable and selectable function, in particular the expression of a chromosomally integrated β-galactosidase gene which is under ctx control. According to the invention, the microorganism is preferably an Escherichia coli strain, in particular FHK11 or FHK12.

For the purposes of the invention, the protein which is capable of ligand binding is selected from immunoglobulins, antigens, receptor domains, receptor ligands, in particular hormones, enzymes and inhibitors.

According to a preferred embodiment of the process according to the invention, the proteins in this context are immunoglobulins, in particular $F_{ab}$ fragments, $F_v$ fragments, single-chain $F_v$ fragments, or monomers or homodimers of light chains. It is furthermore preferred that the transmembrane helix is selected from the transmembrane helices of the ToxR gene of Vibrio cholerae, the protooncogene C-new, the P-new oncogene and membrane-bound IgM. The preferred transcription activator of the process is the N-terminal end, i.e. amino acids 1–182, of the ToxR protein.

The invention furthermore relates to a microorganism which can suitably be used for the genetic selection by transduction and which contains a genetically stable detectable function. In this context, this detectable function is preferably a chromosomally integrated β-galactosidase gene which is under ctx control. The Escherichia coli strains FHK11 and FHK12 are particularly preferred.

Over and above this, a process is disclosed for preparing the abovementioned microorganisms, in which process the detectable function is introduced into the microorganism with the aid of an integration vector.

The, invention furthermore relates to the above-defined replicons, and to their preparation, comprising the. fusion of DNA fragments, encoding transmembrane helix, regulatory domain and protein capable of ligand binding.

BRIEF DESCRIPTION OF THE DRAWINGS

The invention is explained in more detail by the following figures.

CtxLo: (SEQ ID NO: 2)
5'-GTTTTCCCAGTCACGACGACGTTGTAAAACGACAGAATCTGCCCGATATAACTTATC-3'

CtxΔSig: (SEQ ID NO: 3)
5'-CAGCACGTTGTAGTACTACCTTTACCATATA-3' c) ligand-induced homodimer formation and d) ligand-induced heterodimer formation FIG. 2 Diagrammatic representation of the cloning steps for constructing the vector pHKToxREI.

Figure 3:
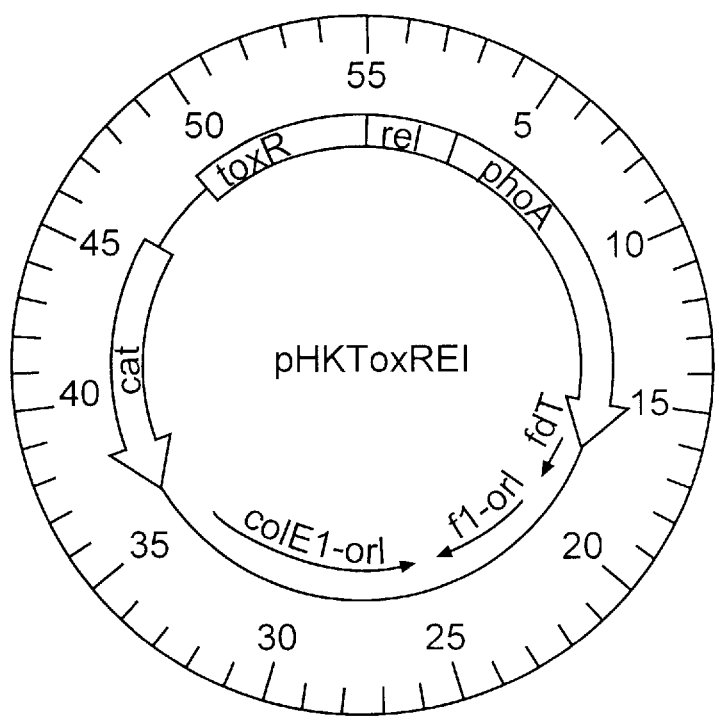

FIG. 3 Physical and genetic map of pHKToxREI. cat: Gene for chloramphenicol acetyltransferase; colE1-ori: ColE1 origin of replication; f1 -ori: bacterio-phage f1 origin of replication; fdT: bacteriophage fd transcription terminators; toxR: promoter-proximal segment of the ToxR gene (promoter including codons 1–210); rei: gene for the immunoglobulin domain REI; phoA: coding sequence for alkaline phosphatase.

Figure 4:
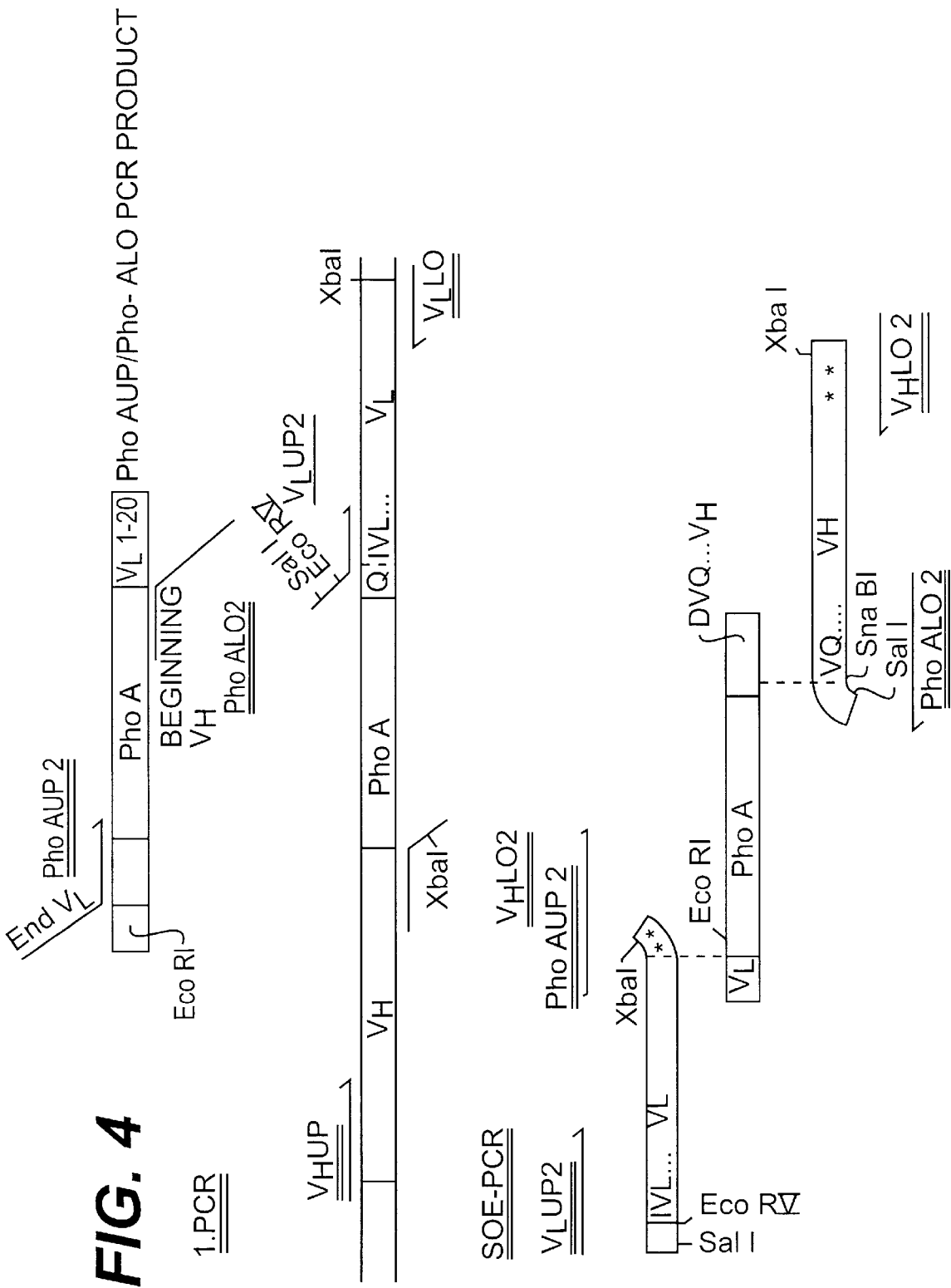

FIG. 4: PCR scheme for preparing the construct $V_L phoAV_H$.

DETAILED DESCRIPTION OF THE INVENTION

Tab. 1: Sequence of the single-chain Fv fragment (scFv) of the phenyloxazolone-binding antibody NQ10.12.5.

Tab. 2: Part of the nucleotide sequence of the construct $poxRV_H pelBV_L$; SD: Shine-Dalgarno sequence; +++++ sequence inserted by PelB1 oligonucleotide; ***** sequence inserted by PelB2 oligonucleotide.

Tab. 3: Sequence of the $V_H phoAV_L$ construct.

Tab. 4: Sequence of the $V_L phoAV_H$ construct.

Tab. 5: Nucleotide sequence of the promoter-proximal segment of the toxR gene; the putative transmembrane helix is underlaid.

Tab. 6: Oligonucleotides employed.

The present invention discloses an experimental system which models in microorganisms important features of the immune system of higher vertebrates. This system can be used for clonal expansion induced by antigen binding and for fine adjustment of antigen recognition by mutation and selection.

The invention will be elucidated in more detail by the following examples.

EXAMPLES

Example I (Strain construction)

1. Construction of FHK11

FHK11: F⁻, ara, Δ(lac-proAB), rpsL, φ80 dΔ(lacZM15), attHB::ctxDsiglacZ

The ctx promoter was amplified from the chromosome of a pathogenic V. cholerae strain by means of PCR using the oligonucleotides CtxUp and ctxLo. The PCR product contains the ctx promoter region possessing a ToxR recognition sequence which is repeated seven times (Miller et al., Cell 48, 271 (1987)). Since the *Escherichia coli* strains described in this publication which possessed a chromosomally integrated ctxlacZ gene fusion exhibited genetic instability, the putative CtxA signal sequence of codons 5 to 28 was removed, in contrast to Miller et al. This removal was effected by reamplifying the ctx promoter using the oligonucleotides CTxUp and CtxΔsig.

The sequences which are complementary to the ctx promoter are emphasized with bold type.

The lacZ gene was subsequently fused to the ctx promoter by means of SOE PCR. The resulting product was cloned as a BamHI fragment into the BamHI-linearized vector pLDR10 (Diederich et al., Plasmid, 28, 14–24 (1992)) in an orientation in which the ctx promoter is arranged in the opposite direction to the promoter of the bla gene, and integrated, in accordance with the method described by Diederich, into the chromosome of the *E. coli* strain JM83.

2. Construction of FHK12

FHK12: F'lacZΔM15, lacY⁺, ProA⁺B⁺ ara, Δ(lac-proAB), rps1, φ80 dΔ (lacZM15), attB::ctxDsiglacZ The F episome of the strain CSH22 (trpR, Δlac-pro, thi, F'lacZΔM15, lacY⁺, ProA⁺B⁺) was transferred from this strain to the strain FHK11 by conjugation. The F episome contains the gene for Lac permease (lacY) and complements the chromosomal pro deletion. It was therefore easy to select conjugants on M9 plates which contained ampicillin. Under these circumstances, FHK12 grew in M9 lactose medium, and on M9 lactose minimal plates, without any activation of the ctx promoter.

Example II (Construction of replicons)

1. Construction of pHKToxREI

The promoter-proximal moiety of the toxR gene (see FIG. 9), which contains the toxR promoter and the portion of the sequence for the first 210 amino acids (V. L. Miller et al.: Cholera toxin transcriptional activator ToxR is a transmembrane DNA binding protein; Cell 48, 271–279 (1987)), was amplified from the cell lysate of a pathogenic V. cholerae strain using the PCR primers IMG212 and IMG142. The reaction product was cut with MluI and PstI and inserted into an MluI/PstI-restricted pBluescript derivative (pBluescript II-pms1'; source, B. Fartmann, Inst. für Molekulare Genetik der Universität Göttingen (Göttingen University Institute of Molecular Genetics)), which possesses unique restriction cleavage sites for BamHI, MluI and PstI (in the given order). The 2 kbp BamHI/PstI fragment containing the segment of toxR gene sequence was isolated out of this construct. In parallel, a SalI/XbaI fragment, which contains a rei-phoA fusion gene (i.e. the gene for the immunoglobulin domain REI, and the gene for alkaline phosphatase), was removed from the vector pHKREI (H. Kolmar et al., J. Mol. Biol. 228, 359–365, (1992)) and inserted into the SalI/XbaI-cleaved vector pMCΔbla (H. Kolmar: On the folding stability of a variant immunoglobulin domain. Eberhard-Karls University, Tübingen, dissertation (1992)). The resulting construct (pMcΔbla-reiphoA) was cut with BamHI and XbaI, and the resulting vector fragment ligated to the above-described BamHI/XbaI fragment containing the segment of ToxR gene sequence. The segment of pms1' sequence which had been incorporated concomitantly was removed by cutting the resulting vector, filling in the ends and religating. A HindIII fragment from pMcΔbla-lacbla-REI (H. Kolmar: loc. cit.), which fragment contains the gene for the immunoglobulin domain REI, was inserted into the unique HindIII cleavage site, lying downstream of the phoA gene, of the resulting vector. Subsequently, the coding sequence of the rei gene (Kolmar et al., 1992) was fused to the coding sequence of the toxR gene (codons 1 to 210), and the intergenic EcoRV cleavage site introduced, by means of site-directed mutagenesis using the oligonucleotide IMG166 recloned as a HindIII/NotI fragment, including the pelB leader sequence located prior to it, into the Bluescript vector pBSK(−), and subjected to nucleotide sequence analysis. Some regions of the cloned scFv gene deviated markedly in their sequence from that of the published NQ10.12.5 sequence (Bearek et al., 1985). This was the case, in particular, for the beginning and the end of the regions encoding $V_H$ and $V_L$. The deviations in these regions are possibly due to the use of degenerate primers in the amplification of these genes from the NQ10.12.5 cell line. Over and above this, two point mutations, which led to amino acid exchanges ($V_H$: 157→L, T77→N; $V_L$:$K^{18}$→R, T48→I), were also found by sequencing in each of the $V_H$ and $V_L$-encoding sequences (in addition to some silent base changes).

The following strategy was used to repair the scFv gene:

The regions encoding $V_H$ and $V_L$ were initially reamplified separately using PCR. By using the PCR primers $V_H$UPCIMG 258)66mer (SEQ ID NO: 7)
CAGCGA<u>GTCGACTACGTA</u>CAGCTGGTGGAGCTTGGGGGAGGCTTTGTGCAGCCTGGAGGGTCCCGG SalI SnaBI $V_H$LO(IMG 256)83mer (SEQ ID NO: 8)
AATTT<u>GGATCC</u>GCCACCGCCAGAGCCACCTCCGCCTGAACCGCCTCCACCTGAGGAGACGGTGAC BamHI $V_L$UP(IMG 257)37mer (SEQ ID NO: 9)
GGTGGC<u>GGATCC</u>CAAATTGTTCTCACCCAGTCTCCAG BamHI $V_L$LO(IMG 259)49mer (SEQ ID NO: 10)
CGCGGT<u>TCTAGA</u>TTATCACCGTTTCAGTTCAAGCTTGGTCCCAGCACCG XbaI (pHKTox-REI).

IMG121: (SEQ ID NO: 4)
CGGGTCATACCGATCCCGTTATCCGAAATGG

IMG142: (SEQ ID NO: 5)
CGACGGTAC<u>CTGCAG</u>CGTTAGGGGTTTAAAGCTGGATTG

PstI

IMG166: (SEQ ID NO: 6)
CATCTGGATATCCGTTAGGGGTTTAAAGC

Relevant restriction cleavage sites are underlined, while the segments of sequence which are complementary to the toxR region from V. cholerae are emphasized with bold type.

Figure 1A:
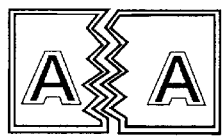
FIGS. 1A to 1D are diagrams of signal transduction by dimer formation as follows: a) not ligand-induced homodimer formation b) not ligand-induced heterodimer formation CtxUp: (SEQ ID NO: 1)
5'-GTGTGTGATACGAAACGAAGCATTGGATCCTAGAAGTGAAACGGGGTTTACCG-3'
Figure 1A:
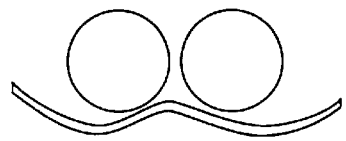
Figure 1B:
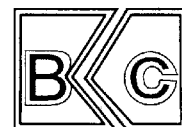
Figure 1B:
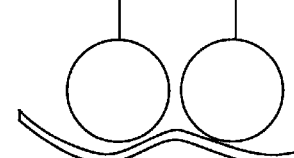
Figure 1C:
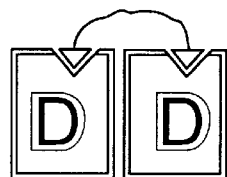
Figure 1C:
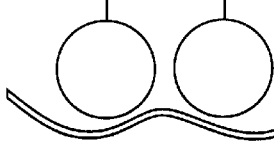
Figure 1D:
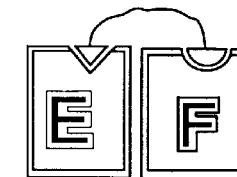
Figure 1D:
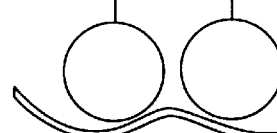
Figure 2:
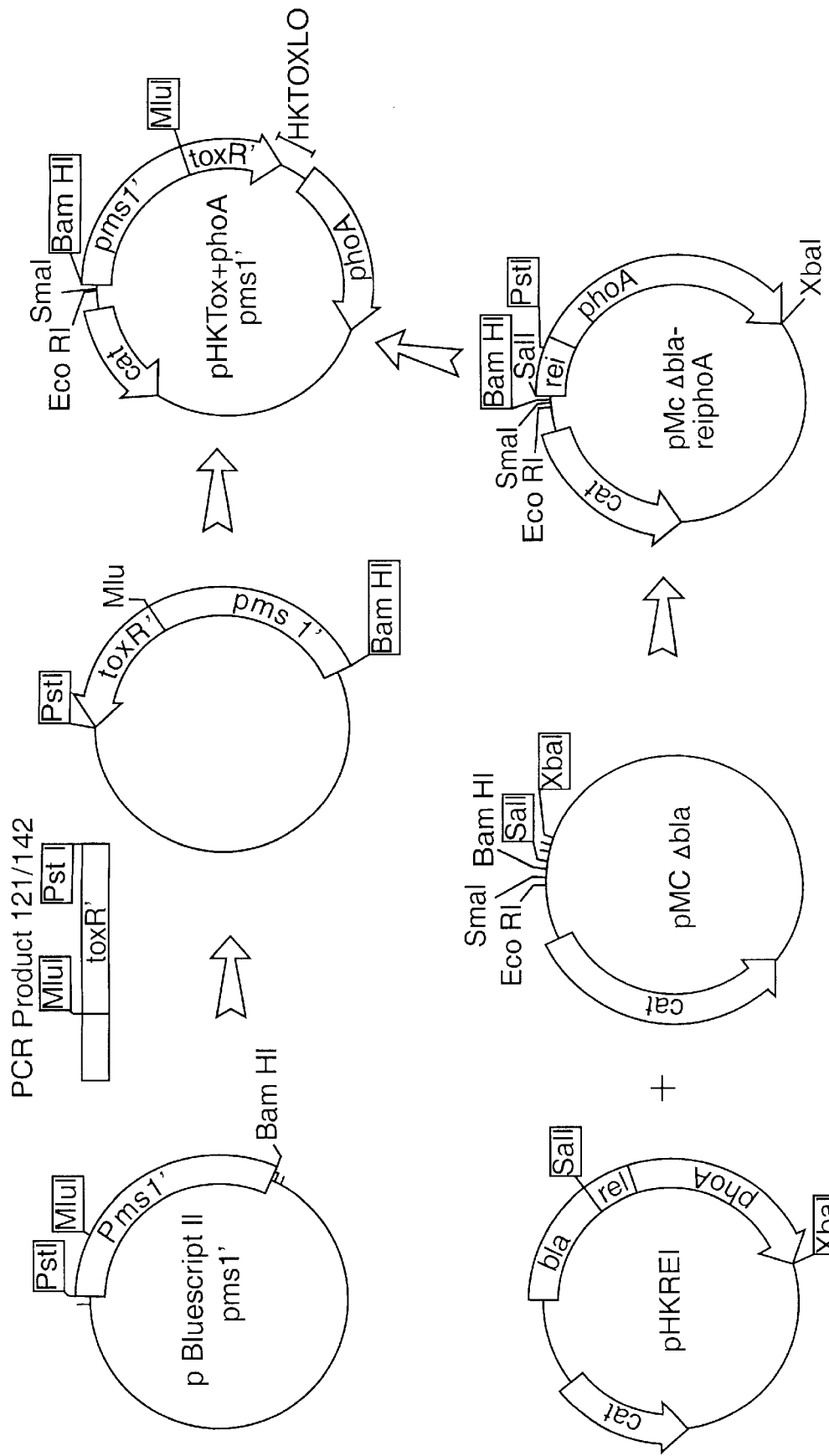

A diagrammatic representation of the above cloning steps used for constructing the vector pHKToxREI is presented in FIG. 2, as is a physical and genetic map of pHK-Tox-REI in FIG. 3.

2. Construction of pHKToxscFv

The single-chain Fv fragment (scFv) of the phenyloxazolone-binding antibody NQ10.12.5 (Berek et al., 1985; Berek and Milstein, 1987; Sequence: see Tab. 1), in which the C terminus of the $V_H$ domain is covalently bound via a short peptide linker [(Gly$_4$Ser)$_3$] to the N terminus of the $V_L$ domain, was made available by Greg Winter's group (MRC, Cambridge) as an SfiI/NotI fragment cloned into the vector pHEN1 (H. R. Hoogenboom et al.: Multisubunit proteins on the surface of filamentous phage: methodologies for displaying antibody (Fab) heavy and light chains; Nucl. Acids Res. 19, 4133–4137 (1991)), in the form of the plasmid pHEN1::NQ10.12.5scFv fragment. It was initially the sequences at the beginning and end of these regions were repaired so that they were brought into line with the NQ10.12.5 sequence. Using the $V_H$UP primer, a SalI cleavage site was introduced upstream of the $V_H$ gene, and using the $V_H$LO primer a BamHI cleavage site was introduced in the region of the sequence encoding the single-chain linker. This BamHI cleavage site was also introduced by the $V_L$UP primer. Finally, an XbaI cleavage site was introduced at the end of the $V_L$ gene by the $V_L$LO primer.

Using these cleavage sites, the amplified fragments were next cloned separately into the pBSK(−) vector (the SnaBI (blunt) cleavage site introduced at the beginning of the $V_H$ gene was required for the subsequent cloning of the scFV gene downstream of the toxR gene, which gene possesses, at its end, an EcoRV cleavage site (likewise blunt)).

Repair of the 4 remaining point mutations was next carried out on the separately cloned fragments using oligonucleotide-directed mutagenesis. Owing to the distance of the individual mutations from each other, a separate repair oligonucleotide had to be defined for each mutagenesis. In order to facilitate screening, the oligonucleotides were defined such that, in addition to effecting mutagenesis repair, they also introduced or destroyed a restriction cleavage site.

Oligonucleotides for repair mutageneses

-continued

V$_H$L571(IMG 260)32mer (SEQ ID NO: 11)
GTCTGCATAGTAGAT<u>AGTACT</u>ACTGCCACTAC

ScaI

V$_H$N77T(IMG 261)34mer (SEQ ID NO: 12)
GACTGGTCAT<u>CTGCAG</u>GAACAGGGTGTTCTTGGG PstI V$_L$R18K(IMG 262)26mer (SEQ ID NO: 13)
GGTCT<u>GGTGAC</u>TTTCTCCCCTGGAG destroyed BstEII site V$_L$148T(IMG 263)34mer (SEQ ID NO: 14)
GGATGTGT<u>CATATG</u>TCC<u>AGCGCT</u>TGGGGGAGGTG NdeI Eco47III The point mutation to be introduced is emphasized with bold type.

Finally, the fragments were once again cloned together using the BamHI cleavage site located in the sequence encoding the single-chain linker.

The NQ10.12.5 scFv gene was cloned, as a SnaBi/XbaI fragment (sequence, see Tab. 1), into the vector pHKToxREI, which had been cut with EcoRV and XbaI. Using EcoRV and XbaI, the sequence encoding REI and PhoA is eliminated from this plasmid. Cloning the scFv gene into the vector pHKToxRei which has been cut with EcoRV and XbaI results in a toxR-scFv fusion gene.

3. Construction of pHKToxV$_H$phoAV$_L$

In addition, a fusion comprising ToxR and the two-chain Fv fragment of the antibody NQ10.12.5 was constructed in which the V$_H$ domain was left at the carboxyl terminus of the ToxR protein while V$_L$ is coexpressed in soluble form. In order to make possible secretion of the V$_L$ protein into the periplasm, the V$_L$ gene had to be provided with the pelB leader sequence (S.-P. Lei et al., (1987): Characterization of the *Erwinia carotovora* pelB Gene and its product pectate lyase; J. Bacteriol. 169, 4379–4383). Removal of the single-chain linker and insertion of the leader were to be effected by means of two consecutive oligonucleotide-directed mutageneses using the oligonucleotides pelB1 and pelB2.

PelB1 (IMG 306) (SEQ ID NO: 15)
GAGAACAATTTGGGCCATGGCTGGTTGGGCAGCGAGTAATAACAATCCAGCGGCTGCCGTGATATCTGAGGA
GACGGTG

PelB2 (IMG 307) (SEQ ID NO: 16)
CAGCGGCTGCCGTAGGCAATAGGTATTTCATTATGACTGTCTCCTTGAAATAGAATTCGCATTATCATGAGG
AGACGGTG

Following the second mutagenesis, a clone was obtained which exhibited the correct restriction pattern. However, analysis of the nucleotide sequence of this clone indicated three deletions, two (1 and 8 nucleotides, respectively) in the sequence encoding the signal peptide and one (1 nucleotide) in the intergenic region between V$_H$ and pelBV$_L$ (see Tab. 2).

The erroneous pelB leader sequence upstream of the V$_L$ gene was then replaced by the leader sequence of alkaline phosphatase (H. Inouye et al.: Signal sequence of alkaline phosphatase of *Escherichia coli*; J. Bacteriol. 149, 434–439, (1982)). The PCR primers PhoASigUP and PhoASigLO were used to amplify the phoA signal sequence from the *E. coli* chromosome.

PhoASigUP (IMG400), 38mer (SEQ ID NO: 17)
TTT<u>GAATTC</u>ATTTGTACATGGAGAAAATAAAGTGAAAC EcoRI PhoASigLO (IMG399), 42mer (SEQ ID NO: 18)
<u>GACTGGGTGAGAACAATTTG</u>GGCTTTTGTCACAGGGGTAAAC homologous to V$_L$ The 5' end of the PhoASigLO primer was homologous to the promoter-proximal region of the V$_L$ gene, so that the phoA fragment could be linked to the V$_L$ gene by means of SOE OPCR. At the 5' end of the PhoASigUP primer, an EcoRI cleavage site was defined with the aid of which the phoA-VL SOE PCR product was cloned downstream of the V$_H$ gene. The sequence of the V$_H$phoAV$_L$ construct is given in Tab. 3.

4. Construction of pHKToxV$_L$phoAV$_H$

PCR was employed to construct pHKToxV$_L$phoAV$_H$, in which the V$_L$ gene was fused to the toxR sequence and V$_H$ was provided with the phoA leader sequence, using the oligonucleotides IMG409–IMG 412 (see Tab. 6).

PhoAUP2 (IMG409), 36mer (SEQ ID NO: 19)
               EcoRI

<u>GAACTGAAACGGTGATAA</u> <u>GAATTC</u>ATTTGTACATGG
    End of V$_L$     Beginning of phoA PhoALO2 (IMG411), 39mer (SEQ ID NO: 20)
<u>CCAAGCTCCACCAGCTGTACATC</u> GGCTTTTGTCACAGGG Beginning of V$_H$ (Asp) End of phoA V$_H$LO2 (IMG412), 28mer (SEQ ID NO: 21)
    XbaI GAATCTAGA TTATCATGAGGAGACGGTG
               End of V$_H$ V$_L$UP2(IMG410), 32mer (SEQ ID NO: 22)
  SalI        EcoRV ACA GTCGAC G<u>ATATC</u> GTTCTCACCCAGTCTCC Ile Beginning of V$_L$ The region encoding the phoA signal sequence (H. Inouye et al.: Signal sequence of alkaline phosphatase of *Escherichia coli*; J. Bacteriol. 149, 434–439 (1982)) was initially amplified using the primers PhoAUP2 and PhoALO2. The PCR product amplified from the *E. coli* chromosome using the primers PhoASigUP and PhoASigLO was used as the template for this (see Example II.3 "Construction of phKToxV$_H$phoAV$_L$"). The 5' terminus of primer PhoAUP2 was complementary to the end of the V$_L$ sequence, while the 5' terminus of primer PhoALO2 was complementary to the first 20 nucleotides of the V$_H$ sequence. The complementary ends were required for the SOE PCR with the V$_H$ and V$_L$ fragments in the next step. Furthermore, the N-terminal aspartate residue of the NQ10.12.5 V$_H$ sequence (P. M. Alzari et al.: Three-dimensional structure determination of an anti-2-phenyloxazolone antibody: the role of somatic mutation and heavy/light chain pairing in the maturation of an immune response; EMBO J., 9, 3807–3814 (1990)), which was lacking in the previous constructs due to practical considerations (requirement for a restriction cleavage site), was reintroduced by the PhoALO2 primer.

The V$_H$ and V$_L$ genes were amplified from the V$_H$PhoAV$_L$ construct using the primers V$_H$UP and V$_H$LO2, and V$_L$UP2 and V$_L$LO, respectively. Primers V$_L$UP2 and V$_H$LO2 introduced the cleavage sites which were necessary for the clonings (SalI and XbaI for cloning into the Bluescript vector pBSK(−), and EcoRV and XbaI for cloning into pHKToxREI). Since a blunt-end cleavage site was required at the beginning of the V$_L$ sequence, it was not possible to amplify the first codon (Gln) at the same time. By replacing the ATT codon#2 by ATC (both encode Ile), it was possible to generate an EcoRV cleavage site. The three PCR products were subsequently linked to each other by SOE PCR. The sequence of the V$_L$phoAV$_H$ construct is depicted in Tab. 4. The SOE PCR product was subsequently cloned, as an EcbRV/XbaI fragment, into the vector pHKToxREI. In this process, the sequence encoding REI and PhoA was removed, and V$_L$ was fused in-frame with the ToxR-encoding sequence.

Example III

Signal transduction by a homodimeric fusion protein comprising the transcription-activating domain of ToxR and an immunoglobulin variable light chain.

The vector pHKToxREI was constructed as described in Example II point 1. This vector contains a fusion gene comprising the transcription-activating domain of ToxR and the gene for the variable immunoglobulin domain of the Bence-Jones protein REI (H. Kolmar et al.: J. Mol. Biol. 228, 359–365 (1992)). The REI domain is a homodimer (Epp et al., Eur. J. Biochem. 45, 513–524, (1974)). As a control, the vector pHKTox-TAG was constructed in which a stop codon was inserted by site-directed mutagenesis between toxR and rei using the oligonucleotide IMG167, so that, in this vector, only the transcription-activating domain, and not the REI domain, is expressed.

IMG167:(SEQ ID NO:23)
5'-CATCTGGATATCCTACCAATGCTTAAT-3'

Following transformation of strain FHK11 with this vector, the activation of the chromosomally integrated ctx promoter which was mediated by dimerization of the extracytoplasmic REI domains was determined by measuring the β-galactosidase activity in the relevant transformations, which had been cultivated overnight at 37° C. While the enzyme activity was 130 Miller units for pHKToxTAG (extracytoplasmic domain lacking), it was 400 Miller units for pHKToxREI, corresponding to an approximately three-fold activation of transcription. This demonstrates that dimerization of the extracytoplasmic immunoglobulin domains can be detected directly by means of the ToxR-mediated signal transduction.

The *E. coli* strain FHK12/pHKToxV$_L$phoAV$_H$ has been deposited in the Deutsche Sammlung von Mikroorganismen und Zellkulturen GmbH (German collection of microorganisms and cell cultures), Maschroder Weg 1b, W3300 Braunschweig, under the designation DSM 8345.

TABLE 1

(SEQ ID NOs: 24, 25, and 41)

CAGCGAGTCGACTACGTACAGCTGGTGGAGCTTGGGGGAGGCTTTGTGCAGCCTGGAGGG  60
GTCGCTCAGCTGATGCATGTCGACCACCTCGAACCCCCTCCGAAACACGTCGGACCTCCC

Q   R   V   D   Y   V   Q   L   V   E   L   G   G   G   F   V   Q   P   G   G

TCCCGGAAACTCTCCTGTGCAGCCTCTGGATTCACTTTCAGTAGCTTTGGAATGCACTGG  120
AGGGCCTTTGAGAGGACACGTCGGAGACCTAAGTGAAAGTCATCGAAACCTTACGTGACC

S   R   K   L   S   C   A   A   S   G   F   T   F   S   S   F   G   M   H   W

CTTCGTCAGGCTCCAGAGAAGGGGCTGGAGTGGGTCGCATATATTAGTAGTGGCAGTAGT  180
CAAGCAGTCCGAGGTCTCTTCCCCGACCTCACCCAGCGTATATAATCATCACCGTCATCA

V   R   Q   A   P   E   K   G   L   E   W   V   A   Y   I   S   S   G   S   S

ACTATCTACTATGCAGACACAGTGAAGGGCCGATTCACCATCTCCAGAGACAATCCCAAG  240
TGATAGATGATACGTCTGTGTCACTTCCCGGCTAAGTGGTAGAGGTCTCTGTTAGGGTTC

T   I   Y   Y   A   D   T   V   K   G   R   F   T   I   S   R   D   N   P   K

AACACCCTGTTCCTGCAGATGACCAGTCTAAGGTCTGAGGACACGGCCATGTATTACTGT  300
TTGTGGGACAAGGACGTCTACTGGTCAGATTCCAGACTCCTGTGCCGGTACATAATGACA

N   T   L   F   L   Q   M   T   S   L   R   S   E   D   T   A   M   Y   Y   C

GCAAGAGATTACGGGGCTTATTGGGGCCAAGGGACCCTGGTCACGTCTCCTCAGGTGGA  360
CGTTCTCTAATGCCCCGAATAACCCCGGTTCCCTGGGACCAGTGGCAGAGGAGTCCACCT

A   R   D   Y   G   A   Y   W   G   Q   G   T   L   V   T   V   S   S   G   G

TABLE 1-continued (SEQ ID NOs: 24, 25, and 41)

```
GGCGGTTCAGGCGGAGGTGGCTCTGGCGGTGGCGGATCCCAAATTGTTCTCACCCAGTCT  420
CCGCCAAGTCCGCCTCCACCGAGACCGCCACCGCCTAGGGTTTAACAAGAGTGGGTCAGA

G   G   S   G   G   G   S   G   G   G   S   Q   I   V   L   T   Q   S

CCAGCAATCATGTCTGCATCTCCAGGGGAGAAAGTCACCATGACCTGCAGTGCCAGTTCA   480
GGTCGTTAGTACAGACGTAGAGGTCCCCTCTTTCAGTGGTACTGGACGTCACGGTCAAGT

P   A   I   M   S   A   S   P   G   E   K   V   T   M   T   C   S   A   S   S

AGTGTAAGGTACATGAACTGGTTCCAACAGAAGTCAGGCACCTCCCCCAAGCGCTGGACA   540
TCACATTCCATGTACTTGACCAAGGTTGTCTTCAGTCCGTGGAGGGGGTTCGCGACCTGT

S   V   R   Y   M   N   W   F   Q   Q   K   S   G   T   S   P   K   R   W   T

TATGACACATCCAAACTGTCTTCTGGAGTCCCTGCTCGCTTCAGTGGCAGTGGGTCTGGG   600
ATACTGTGTAGGTTTGACAGAAGACCTCAGGGACGAGCGAAGTCACCGTCACCCAGACCC

Y   D   T   S   K   L   S   S   G   V   P   A   R   F   S   G   S   G   S   G

ACCTCTTACTCTCTCACAATCAGCAGCATGGAGGCTGAAGATGCTGCCACTTATTACTGC   660
TGGAGAATGAGAGAGTGTTAGTCGTCGTACCTCCGACTTCTACGACGGTCAATAATGACG

T   S   T   S   L   T   I   S   S   M   E   A   E   D   A   A   T   Y   Y   C

CAGCAGTGGAGTAGTAATCCACTCACTTTCGGTGCTGGGACCAAGCTTGAACTGAAACGG   720
GTCGTCACCTCATCATTCGGTGAGTGAAAGCCACGACCCTGGTTCGAACTTGACTTTGCC

Q   Q   W   S   S   N   P   L   T   F   G   A   G   T   K   L   E   L   K   R

TGATAATCTAGAACCGAG   738
ACTATTAGATCTTGGCGC

*   * wherein the amino acid sequence is

Gln Arg Val Asp Tyr Val Gln Leu Val Glu Leu Gly Gly Gly Phe Val
 1           5                  10                  15

Gln Pro Gly Gly Ser Arg Lys Leu Ser Cys Ala Ala Ser Gly Phe Thr
            20                  25                  30

Phe Ser Ser Phe Gly Met His Trp Val Arg Gln Ala Pro Glu Lys Gly
        35                  40                  45

Leu Glu Trp Val Ala Tyr Ile Ser Ser Gly Ser Ser Thr Ile Tyr Tyr
    50                  55                  60

Ala Asp Thr Val Lys Gly Arg Phe Thr Ile Ser Arg Asp Asn Pro Lys
65                  70                  75                  80

Asn Thr Leu Phe Leu Gln Met Thr Ser Leu Arg Ser Glu Asp Thr Ala
                85                  90                  95

Met Tyr Tyr Cys Ala Arg Asp Tyr Gly Ala Tyr Trp Gly Gln Gly Thr
                100                 105                 110

Leu Val Thr Val Ser Ser Gly Gly Gly Ser Gly Gly Gly Gly Ser
                115                 120                 125

Gly Gly Gly Gly Ser Gln Ile Val Leu Thr Gln Ser Pro Ala Ile Met
    130                 135                 140

Ser Ala Ser Pro Gly Glu Lys Val Thr Met Thr Cys Ser Ala Ser Ser
145                 150                 155                 160

Ser Val Arg Tyr Met Asn Trp Phe Gln Gln Lys Ser Gly Thr Ser Pro
                165                 170                 175
```

TABLE 1-continued (SEQ ID NOs: 24, 25, and 41)

| Lys | Arg | Trp | Thr 180 | Tyr | Asp | Thr | Ser | Lys 185 | Leu | Ser | Ser | Gly | Val 190 | Pro | Ala |

| Arg | Phe | Ser 195 | Gly | Ser | Gly | Ser | Gly 200 | Thr | Ser | Tyr | Ser | Leu 205 | Thr | Ile | Ser |

| Ser | Met | Glu 210 | Ala | Glu | Asp | Ala 215 | Ala | Thr | Tyr | Tyr | Cys 220 | Gln | Gln | Trp | Ser |

| Ser 225 | Asn | Pro | Leu | Thr | Phe 230 | Gly | Ala | Gly | Thr | Lys 235 | Leu | Glu | Leu | Lys | Arg 240 |

TABLE 2

(SEQ ID NOs. 26, 27, 28, and 42)

```
GCAAGAGATTACGGGGCTTATTGGGGCCAAGGGACCCTGGTCACCGTCTCCTCATGATAA  360
CGTTCTCTAATGCCCCGAATAACCCCGGTTCCCTGGGACCAGTGGCAGAGGAGTACTATT
                                                      * * * * * *

A   R   D   Y   G   A   Y   W   G   Q   G   T   L   V   T   V   S   S  |*   *
                                                           EndeV →
                                                                 H EcoRI                SD
TGCGAATTCTATTTCAAGGAGACAGTCATAATGAAATACCTATTGCCTACGGCAGCCGCT  420
ACGCTTAAGATAAAGTTCCTCTGTCAGTATTACTTTATGGATAACGGATGCCGTCGGCGA

* * * * * * * * * * * * * * * * * * * * * * * * * * * * * * * * * * * + + + + + + + + + + +
                                        |M   K   Y   L   L   P   T   A   A   A
                                        |→PelB-Leader GGATTGTTATTACTCGCTGCCCAACCAGCCATGGCCCAAATTGTTCTCACCCAGTCTCCA  480
CCTAACAATAATGAGCGACGGGTTGGTCGGTACCGGGTTTAACAAGAGTGGGTCAGAGGT

+ + + + + + + + + + + + + + + + + + + + + + + + + + + + + + + + + + + +

G   L   L   L   A   A   Q   P   A   M   A  |Q   I   V   L   T   Q   S   P
                                            |→ Beginn   V
                                                        L
``` wherein the amino acid sequence is

| Ala 1 | Arg | Asp | Tyr 5 | Gly | Ala | Tyr | Trp 10 | Gly | Gln | Gly | Thr 15 | Leu | Val | Thr | Val |
| Ser | Ser |

| Met 1 | Lys | Tyr | Leu 5 | Leu | Pro | Thr | Ala 10 | Ala | Ala | Gly 15 | Leu | Leu | Leu | Leu | Ala |
| Ala | Gln | Pro 20 | Ala | Met | Ala | Gln 25 | Ile | Val | Leu | Thr 30 | Gln | Ser | Pro |

TABLE 3

(SEQ ID NOS. 29, 30, 31, and 43)

```
CAGCGAGTCGACTACGTACAGCTGGTGGAGCTTGGGGGAGGCTTTGTGCAGCCTGGAGGG   60
GTCGCTCAGCTGATGCATGTCGACCACCTCGAACCCCCTCCGAAACACGTCGGACCTCCC

V   Q   L   V   E   L   G   G   G   F   V   Q   P   G   G

TCCCGGAAACTCTCCTGTGCAGCCTCTGGATTCACTTTCAGTAGCTTTGGAATGCACTGG  120
AGGGCCTTTGAGAGGACACGTCGGAGACCTAAGTGAAAGTCATCGAAACCTTACGTGACC

S   R   K   L   S   C   A   A   S   G   F   T   F   S   S   F   G   M   H   W

GTTCGTCAGGCTCCAGAGAAGGGGCTGGAGTGGGTCGCATATATTAGTAGTGGCAGTAGT  160
CAAGCAGTCCGAGGTCTCTTCCCCGACCTCACCCAGCGTATATAATCATCACCGTCATCA

V   R   Q   A   P   E   K   G   L   E   W   V   A   Y   I   S   S   G   S   S
```

TABLE 3-continued (SEQ ID NOS. 29, 30, 31, and 43)

```
ACTATCTACTATGCAGACACAGTGAAGGGCCGATTCACCATCTCCAGAGACAATCCCAAG   240
TGATAGATGATACGTCTGTGTCACTTCCCGGCTAAGTGGTAGAGGTCTCTGTTAGGGTTC

T   I   Y   Y   A   D   T   V   K   G   R   E   I   I   S   R   D   N   P   K

AACACCCTGTTCCTGCAGATGACCAGTCTAAGGTCTGAGGACACGGCCATGTATTACTGT   300
TTGTGGGACAAGGACGTCTACTGGTCAGATTCCAGACTCCTGTGCCGGTACATAATGACA

N   T   L   F   L   Q   M   T   S   L   R   S   E   D   T   A   M   Y   Y   C

GCAAGAGATTACGGGGCTTATTGGGGCCAAGGGACCCTGGTCACCGTCTCCTCATGATAA   360
CGTTCTCTAATGCCCCGAATAACCCCGGTTCCCTGGGACCAGTGGCAGAGGAGTACTATT

A   R   D   Y   G   A   Y   W   G   Q   G   T   L   V   T   V   S   S   *   *

TGCGAATTCATTTGTACATGGAGAAAATAAAGTGAAACAAAGCACTATTGCACTGGCACT   420
ACGCTTAAGTAAACATGTACCTCTTTTATTTCACTTTGTTTCGTGATAACGTGACCGTGA

V   K   Q   S   T   I   A   L   A   L

CTTACCGTTACTGTTTACCCCTGTGACAAAAGCCCAAATTGTTCTCACCCAGTCTCCAGC   480
GAATGGCAATGACAAATGGGACACTGTTTTCGGGTTTAACAAGAGTGGGTCAGAGGTCG

L   P   L   L   F   T   P   V   T   K   A   Q   I   V   L   T   Q   S   P   A

AATCATGTCTGCATCTCCAGGGGAGAAAGTCACCATGACCTGCAGTGCCAGTTCAAGTGT   540
TTAGTACAGACGTAGAGGTCCCCTCTTTCAGTGGTACTGGACGTCACGGTCAAGTTCACA
 I   M   S   A   S   P   G   E   K   V   T   M   T   C   S   A   S   S   S   V

AAGGTACATGAACTGGTTCCAACAGAAGTCAGGCACCTCCCCCAAGCGCTGGACATATGA   600
TTCCATGTACTTGACCAAGGTTGTCTTCAGTCCGTGGAGGGGGTTCGCGACCTGTATACT

R   Y   M   N   W   F   Q   Q   K   S   G   T   S   P   K   R   W   T   Y   D

CACATCCAAACTGTCTTCTGGAGTCCCTGCTCGCTTCAGTGGCAGTGGGTCTGGGACCTC   660
GTGTAGGTTTGACAGAAGACCTCAGGGACGAGCGAAGTCACCGTCACCCAGACCCTGGAG

T   S   K   L   S   S   G   V   P   A   R   F   S   G   S   G   S   G   T   S

TTACTCTCTCACAATCAGCAGCATGGAGGCTGAAGATGCTGCCACTTATTACTGCCAGCA   720
AATGAGAGAGTGTTAGTCGTCGTACCTCCGACTTCTACGACGGTGAATAATGACGGTCGT

Y   S   L   T   I   S   S   M   E   A   E   D   A   A   T   Y   Y   C   Q   Q

GTGGAGTAGTAATCCACTCACTTTCGGTGCTGGGACCAAGCTTGAACTGAAACGGTGATA   780
CACCTCATCATTAGGTGAGTGAAAGCCACGACCCTGGTTCGAACTTGACTTTGCCACTAT

W   S   S   N   P   L   T   F   G   A   G   T   K   L   E   L   K   R   *   *

ATCTAGAACCGCG    793
TAGATCTTGGCGC
``` wherein the amino acid sequence is

| Val | Glu | Leu | Val | Glu | Leu | Gly | Gly | Gly | Phe | Val | Gln | Pro | Gly | Gly | Ser |
|-----|-----|-----|-----|-----|-----|-----|-----|-----|-----|-----|-----|-----|-----|-----|-----|
| 1   |     |     |     | 5   |     |     |     | 10  |     |     |     |     | 15  |     |     |
| Arg | Lys | Leu | Ser | Cys | Ala | Ala | Ser | Gly | Phe | Thr | Phe | Ser | Ser | Phe | Gly |
|     |     | 20  |     |     |     |     | 25  |     |     |     |     | 30  |     |     |     |
| Met | His | Trp | Val | Arg | Gln | Ala | Pro | Glu | Lys | Gly | Leu | Glu | Trp | Val | Ala |
|     | 35  |     |     |     |     | 40  |     |     |     |     | 45  |     |     |     |     |
| Tyr | Ile | Ser | Ser | Gly | Ser | Ser | Thr | Ile | Tyr | Tyr | Ala | Asp | Thr | Val | Lys |
| 50  |     |     |     | 55  |     |     | 60  |     |     |     |     | 65  |     |     |     |
| Gly | Arg | Phe | Thr | Ile | Ser | Arg | Asp | Asn | Pro | Lys | Asn | Thr | Leu | Phe | Leu |
|     |     |     | 70  |     |     |     |     | 75  |     |     |     |     | 80  |     |     |
| Gln | Met | Thr | Ser | Leu | Arg | Ser | Glu | Asp | Thr | Ala | Met | Tyr | Tyr | Cys | Ala |
|     |     |     | 85  |     |     |     |     | 90  |     |     |     |     | 95  |     |     |
| Arg | Asp | Tyr | Gly | Ala | Tyr | Trp | Gly | Gln | Gly | Thr | Leu | Val | Thr | Val | Ser |
|     |     |     | 100 |     |     |     |     | 105 |     |     |     |     | 110 |     |     |
| Ser |     |     |     |     |     |     |     |     |     |     |     |     |     |     |     |

| Val | Lys | Gln | Ser | Thr | Ile | Ala | Leu | Ala | Leu | Leu | Pro | Leu |
|-----|-----|-----|-----|-----|-----|-----|-----|-----|-----|-----|-----|-----|
| 1   |     |     |     | 5   |     |     |     |     | 10  |     |     | 15  |

TABLE 3-continued (SEQ ID NOS. 29, 30, 31, and 43)

| Leu | Phe | Thr | Pro 20 | Val | Thr | Lys | Ala | Gln 25 | Ile | Val | Leu | Thr | Gln 30 | Ser | Pro |
| --- | --- | --- | --- | --- | --- | --- | --- | --- | --- | --- | --- | --- | --- | --- | --- |
| Ala | Ile | Met 35 | Ser | Ala | Ser | Pro | Gly 40 | Glu | Lys | Val | Thr | Met 45 | Thr | Cys | Ser |
| Ala | Ser 50 | Ser | Ser | Val | Arg | Tyr 55 | Met | Asn | Trp | Phe | Gln 60 | Gln | Lys | Ser | Gly |
| Thr 65 | Ser | Pro | Lys | Arg | Trp 70 | Thr | Tyr | Asp | Thr | Ser 75 | Lys | Leu | Ser | Ser | Gly 80 |
| Val | Pro | Ala | Arg | Phe 85 | Ser | Gly | Ser | Gly | Ser 90 | Gly | Thr | Ser | Tyr | Ser 95 | Leu |
| Thr | Ile | Ser | Ser 100 | Met | Glu | Ala | Glu | Asp 105 | Ala | Ala | Thr | Tyr | Tyr 110 | Cys | Gln |
| Gln | Trp | Ser 115 | Ser | Asn | Pro | Leu | Thr 120 | Phe | Gly | Ala | Gly | Thr 125 | Lys | Leu | Glu |
| Leu | Lys 130 | Arg | | | | | | | | | | | | | |

TABLE 4

(SEQ ID NOs. 32, 33, 34 and 44)

```
ACAGTCGACGATATCGTTCTCACCCAGTCTCCAGCAATCATGTCTGCATCTCCAGGGGAG    60
TGTCAGCTGCTATAGCAAGAGTGGGTCAGAGGTCGTTAGTACAGACGTAGAGGTCCCCTC

I   V   L   T   Q   S   P   A   I   M   S   A   S   P   G   E

AAAGTCACCATGACCTGCAGTGCCAGTTCAAGTGTAAGGTACATGAACTGGTTCCAACAG   120
TTTCAGTGGTACTGGACGTCACGGTCAAGTTCACATTCCATGTACTTGACCAAGGTTGTC

K   V   T   M   T   C   S   A   S   S   S   V   R   Y   M   N   W   F   Q   Q

AAGTCAGGCACCTCCCCCAAGCGCTGGACATATGACACATCCAAACTGTCTTCTGGAGTC   180
TTCAGTCCGTGGAGGGGGTTCGCGACCTGTATACTGTGTAGGTTTGACAGAAGACCTCAG

K   S   G   T   S   P   K   R   W   T   Y   D   T   S   K   L   S   S   G   V

CCTGCTCGCTTCAGTGGCAGTGGGTCTGGGACCTCTTACTCTCTCACAATCAGCAGCATG   240
GGACGAGCGAAGTCACCGTCACCCAGACCCTGGAGAATGAGAGAGTGTTAGTCGTCGTAC

P   A   R   F   S   G   S   G   S   G   T   S   Y   S   L   T   I   S   S   M

GAGGCTGAAGATGCTGCCACTTATTACTGCCAGCAGTGGAGTAGTAATCCACTCACTTTC   300
CTCCGACTTCTACGACGGTGAATAATGACGGTCGTCACCTCATCATTAGGTGAGTGAAAG

E   A   E   D   A   A   T   Y   Y   C   Q   Q   W   S   S   N   P   L   T   F

GGTGCTGGGACCAAGCTTGAACTGAAACGGTGATAAGAATTCATTTGTACATGGAGAAAA   360
CCACGACCCTGGTTCGAACTTGACTTTGCCACTATTCTTAAGTAAACATGTACCTCTTTT

G   A   G   T   K   L   E   L   K   R   *   *

TAAAGTGAAACAAAGCACTATTGCACTGGCACTCTTACCGTTACTGTTTACCCCTGTGAC   420
ATTTCACTTTGTTTCGTGATAACGTGACCGTGAGAATGGCAATGACAAATGGGGACACTG

V   K   Q   S   T   I   A   L   A   L   L   P   L   L   F   T   P   V   T

AAAAGCCGATGTACAGCTGGTGGAGCTTGGGGGAGGCTTTGTGCAGCCTGGAGGGTCCCG   480
TTTTCGGCTACATGTCGACCACCTCGAACCCCCTCCGAAACACGTCGGACCTCCCAGGGC

K   A   D   V   Q   L   V   E   L   G   G   G   F   V   Q   P   G   G   S   R
```

TABLE 4-continued (SEQ ID NOs. 32, 33, 34 and 44)

GAAACTCTCCTGTGCAGCCTCTGGATTCACTTTCAGTAGCTTTGGAATGCACTGGGTTCG 540
CTTTGAGAGGACACGTCGGAGACCTAAGTGAAAGTCATCGAAACCTTACGTGACCCAAGC

K   L   S   C   A   A   S   G   F   T   F   S   S   F   G   M   H   W   V   R

TCAGGCTCCAGAGAAGGGGCTGGAGTGGGTCGCATATATTAGTAGTGGCAGTAGTACTAT 600
AGTCCGAGGTCTCTTCCCCGACCTCACCCAGCGTATATAATCATCACCGTCATCATGATA

Q   A   P   E   K   G   L   E   W   V   A   Y   I   S   S   G   S   S   T   I

CTACTATGCAGACACAGTGAAGGGCCGATTCACCATCTCCAGAGACAATCCCAAGAACAC 660
GATGATACGTCTGTGTCACTTCCCGGCTAAGTGGTAGAGGTCTCTGTTAGGGTTCTTGTG

Y   Y   A   D   T   V   K   G   R   F   T   I   S   R   D   N   P   K   N   T

CCTGTTCCTGCAGATGACCAGTCTAAGGTCTGAGGACACGGCCATGTATTACTGTGCAAG 720
GGACAAGGACGTCTACTGGTCAGATTCCAGACTCCTGTGCCGGTACATAATGACACGTTC

L   F   L   Q   M   T   S   L   R   S   E   D   T   A   M   Y   Y   C   A   R

AGATTACGGGGCTTATTGGGGCCAAGGGACCCTGGTCACCGTCTCCTCATGATAATCTAG 780
TCTAATGCCCCGAATAACCCCGGTTCCCTGGGACCAGTGGCAGAGGAGTACTATTAGATC

D   Y   G   A   Y   W   G   Q   G   T   L   V   T   V   S   S   *   *

ATTC 784
TAAG wherein the amino acid sequence is
Ile Val Leu Thr Gln Ser Pro Ala Ile Met Ser Ala Ser Pro Gly Glu
 1               5                  10                  15

Lys Val Thr Met Thr Cys Ser Ala Ser Ser Ser Val Arg Tyr Met Asn
            20                  25                  3 0

Trp Phe Gln Gln Lys Ser Gly Thr Ser Pro Lys Arg Trp Thr Tyr Asp
        35                  40                  45

Thr Ser Lys Leu Ser Ser Gly Val Pro Ala Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Leu Thr Phe
                85                  90                  95

Gly Ala Gly Thr Lys Leu Glu Leu Lys Arg
            100                 105

Val Lys Gln Ser Thr Ile Ala Leu Ala Leu Leu Pro Leu Leu Phe Thr
 1               5                  10                  15

Pro Val Thr Lys Ala Asp Val Gln Leu Val Glu Leu Gly Gly Gly Phe
            20                  25                  30

Val Gln Pro Gly Gly Ser Arg Lys Leu Ser Cys Ala Ala Ser Gly Phe
        35                  40                  45

Thr Phe Ser Ser Phe Gly Met His Trp Val Arg Gln Ala Pro Glu Lys
    50                  55                  60

Gly Leu Glu Trp Val Ala Tyr Ile Ser Ser Gly Ser Ser Thr Ile Tyr
65                  70                  75                  80

Tyr Ala Asp Thr Val Lys Gly Arg Phe Thr Ile Ser Arg Asp Asn Pro
                85                  90                  95

Lys Asn Thr Leu Phe Leu Gln Met Thr Ser Leu Arg Ser Glu Asp Thr
            100                 105                 110

Ala Met Tyr Tyr Cys Ala Arg Asp Tyr Gly Ala Tyr Trp Gly Gln Gly
        115                 120                 125

TABLE 4-continued (SEQ ID NOs. 32, 33, 34 and 44)

```
Thr Leu Val Thr Val Ser Ser
 130             135
```

TABLE 5

(SEQ ID NOs. 35, 36 and 45)

```
    MluI
XACGCGTTTCTTTATTAGTGGTTGCAGTCTCGCTCATAATCGCTCCGTTTACTTCTGTTT    60
XTGCGCAAAGAAATAATCACCAACGTCAGAGCGAGTATTAGCGAGGCAAATGAAGACAAA
               HKtoxup
CAAACAATTGATCCATTGAGACTCAATGGAATTACCTTGATGTGCAAGTGAGATATGGAC   120
GTTTGTTAACTAGGTAACTCTGAGTTACCTTAATGGAACTACACGTTCACTCTATACCTG
            htpG AAAAAATGTAAATTCAAGGTCAAAACTCATAAAAACACTGTTTTTTGATCGAGATTGGAT   180
TTTTTTACATTTAAGTTCCAGTTTTGAGTATTTTTGTGACAAAAAACTAGCTCTAACCTA TATTCTAAGTCTGCATTTTTATCAAAGAAGATAAAAAAACCAGTAAAGTCTGAGTGTTGG   240
ATAAGATTCAGACGTAAAAATAGTTTCTTCTATTTTTTTGGTCATTTCAGACTCACAACC EcoRV
             toxR                                       ClaI
GACAGGGAGATACTGGGACATTAGATGTTCGGATTAGGACACAACTCAAAAGAGATATCG   300
CTGTCCCTCTATGACCCTGTAATCTACAAGCCTAATCCTGTGTTGAGTTTTCTCTATAGC
                          Met Phe Gly Leu Gly His Asn Ser Lys Glu Ile  Ser ATGAGTCATATTGGTACTAAATTCATTCTTGCTGAAAAATTTACCTTCGATCCCCTAAGC   360
TACTCAGTATAACCATGATTTAAGTAAGAACGACTTTTTAAATGGAAGCTAGGGGATTCG ←
Met Ser His Ile  Gly Thr Lys Phe Ile  Leu Ala Glu Lys Phe Thr Phe Asp Pro Leu Ser
                                                       ToxSQ2

AATACTCTGATTGACAAAGAAGATAGTGAAGAGATCATTCGATTAGGCAGCAACGAAAGC   420
TTATGAGACTAACTGTTTCTTCTATCACTTCTCTAGTAAGCTAATCCGTCGTTGCTTTCG
Asn Thr Leu Ile  Asp Lys Gly Asp Ser Glu Glu Ile  Ile  Arg Leu Gly Ser Asn Glu Ser

EcoRI
CGAATTCTTTGGCTGCTGGCCCAACGTCCAAACGAGGTGATTTCTCGCAATGATTTGCAT   480
GCTTAAGAAACCGACGACCGGGTTGCAGGTTTGCTCCACTAAAGAGCGTTACTAAACGTA
Arg Ile  Leu Trp Leu Leu Ala Gln Arg Pro Asn Glu Val Ile  Ser Arg Asn Asp Leu His

GACTTTGTTTGGCGAGAGCAAGGTTTTGAAGTCGATGATTCCAGCTTAACCCAAGCCATT   540
CTGAAACAAACCGCTCTCGTTCCAAAACTTCAGCTACTAAGGTCGAATTGGGTTCGGTAA
Asp Phe Val Trp Arg Glu Gln Gly Phe Glu Val Asp Asp Ser Ser Leu Thr Gln Ala Ile

TCGACTCTGCGCAAAATGCTCAAAGATTCGACAAAGTCCCCACAATACGTCAAAACGGTT   600
AGCTGAGACGCGTTTTACGAGTTTCTAAGCTGTTTCAGGGGTGTTATGCAGTTTTGCCAA
                                                         ←
Ser Thr Leu Arg Lys Met Leu Lys Asp Ser Thr Lys Ser Pro Gln Tyr Val Lys Thr Val

NruI
CCGAAGCGCGGTTACCAATTGATCGCCCGAGTGGAAACGGTTGAAGAAGAGATGGCTCGC   660
GGCTTCGCGCCAATGGTTAACTAGCGGGCTCACCTTTGCCAACTTCTTCTCTACCGAGCG
Pro Lys Arg Gly Tyr Gln Leu Ile  Ala Arg Val Glu Thr Val Glu Glu Glu Met Ala Arg
   HKToxSQ1

GAAAACGAAGCTGCTCATGACATCTCTCAGCCAGAATCTGTCAATGAATACGCAGAATCA   720
CTTTTGCTTCGACGAGTACTGTAGAGAGTCGGTCTTAGACAGTTACTTATGCGTCTTAGT
Glu Asn Glu Ala Ala His Asp Ile  Ser Gln Pro Glu Ser Val Asn Glu Tyr Ala Glu Ser

AGCAGTGTGCCTTCATCAGCCACTGTAGTGAACACACCGCAGCCAGCCAATGTCGTGGCC   780
TCGTCACACGGAAGTAGTCGGTGACATCACTTGTGTGGCGTCGGTCGGTTACAGCACCGG
Ser Ser Val Pro Ser Ser Ala Thr Val Val Asn Thr Pro Gln Pro Ala Asn Val Val Ala
```

TABLE 5-continued (SEQ ID NOs. 35, 36 and 45)

```
AATAAATCGGCTCCAAACTTGGGGAATCGACTGTTTATTCTGATAGCGGTCTTACTTCCC   840
TTATTTAGCCGAGGTTTGAACCCCTTAGCTGACAAATAAGACTATCGCCAGAATGAAGGG
Asn Lys Ser Ala Pro Asn Leu Gly Asn Arg Leu Phe Ile  Leu Ile  Ala Val Leu Leu Pro
                                      ‾‾‾‾‾‾‾‾‾‾‾‾‾‾‾‾‾‾‾‾‾‾‾‾‾‾‾‾‾‾‾‾‾‾‾‾‾‾‾‾‾‾ phoA →

CTCGCAGTATTACTGCTCACTAACCCAAGCCAATCCAGCTTTAAACCCCTAACGCCTGTT   900
GAGCGTCATAATGACGAGTGATTGGGTTCGGTTAGGTCGAAATTTGGGGATTGCGGACAA

←‾‾‾‾‾‾‾‾‾‾‾‾‾‾‾‾‾‾‾‾‾‾‾‾‾‾‾‾‾‾‾‾‾‾
Leu Ala Val Leu Leu Leu  Thr Asn Pro Ser Gln Ser Ser Phe Lys Pro Leu Thr Pro Val
‾‾‾‾‾‾‾‾‾‾‾‾‾‾‾‾‾‾‾‾‾‾‾                       HKToxLo

CTGGAAAACCGGGCTGCTCAGGGCGATATTACTGCACCCGGCGGTGCTCGCCGTTTAACG   960
GACCTTTTGGCCCGACGAGTCCCGCTATAATGACGTGGGCCGCCACGAGCGGCAAATTGC

HKToxLo       ←‾‾‾‾‾‾‾‾‾‾‾‾‾‾‾‾‾‾‾‾‾‾‾
Leu Glu Asn Arg Ala Ala Gln Gly Asp Ile  Thr Ala Pro Gly Gly Ala Arg Arg Leu Thr
                       HKREISQ3
```

TABLE 6

| | | |
|---|---|---|
| (SEQ ID NO:4) IMG121: | CGGGTCATACCGATCCCGTTATCCGAAATGG | |
| (SEQ ID NO:5) IMG142: | CGACGGTACCTGCAGCGTTAGGGGTTTAAAGCTGGATTG | |
| (SEQ ID NO:6) IMG166: | CATCTGGATATCCGTTAGGGGTTTAAAGC | |
| (SEQ ID NO:23) IMG167: | CATCTGGATATCCTACCAATGCTTAAT | |
| (SEQ ID NO:8) IMG256: | AATTTGGGATCCGCCACCGCCAGAGCCACCTCCGCCTGAACCGCCTCC ACCTGAGGAGACGGTGACCAGGGTCCCTTGGCCCC | |
| (SEQ ID NO:9) IMG257: | GGTGGCGGATCCCAAATTGTTCTCACCCAGTCTCCAG | |
| (SEQ ID NO:7) IMG258: | CAGCGAGTCGACTACGTACAGCTGGTGGAGCTTGGGGGAGGCTTTGTG CAGCCTGGAGGGTCCCGG | |
| (SEQ ID NO:10) IMG259: | CGCGGTTCTAGATTATCACCGTTTCAGTTCAAGCTTGGTCCCAGCACCG | |
| (SEQ ID NO:11) IMG260: | GTCTGCATAGTAGATAGTACTACTGCCACTAC | |
| (SEQ ID NO:12) IMG261: | GACTGGTCATCTGCAGGAACAGGGTGTTCTTGGG | |
| (SEQ ID NO:13) IMG262: | GGTCATGGTGACTTTCTCCCCTGGAG | |
| (SEQ ID NO:14) IMG263: | GGATGTGTCATATGTCCAGCGCTTGGGGGAGGTG | |
| (SEQ ID NO:15) IMG306: | CAGAACAATTTGGGCCATGGCTGGTTGGGCAGCGAGTAATAACAATCC AGCGGCTGCCGTGATATCTGAGGAGACGGTG | |
| (SEQ ID NO:16) IMG307: | CAGCGGCTGCCGTAGGCAATAGGTATTTCATTATGACTGTCTCCTTGA AATAGAATTCGCATTATCATGAGGAGACGGTG. | |
| (SEQ ID NO:37) IMG329: | CACGACGTTGTAGTACTACCTTTACCATATA | |
| (SEQ ID NO:38) IMG385: | TTGGCTTGGGTTGATCAGGATCCCAAGCTAGCTCGATTCCCCAAG | |
| (SEQ ID NO:39) IMG388: | TCGAGCTAGCCCGGTTACCTTCATCATCGCTACCGTTGAAGGAGT ACTGC | |

Fortsetzung Tab. 6

| | | |
|---|---|---|
| (SEQ ID NO:40) IMG390: | ATCAGGATCCCAACCACGACAACCAGGATCAGGAACAGCAGTACTCCAA CAACGGTAGC | |
| (SEQ ID NO:18) IMG399: | GACTGGGTGAGAACAATTTGGGCTTTTGTCACAGGGGTAAAC | |
| (SEQ ID NO:17) IMG400: | TTTGAATTCATTTGTACATGGAGAAAATAAAGTGAAAC | |
| (SEQ ID NO:19) IMG409: | GAACTGAAACGGTGATAAGAATTCATTTGTACATGG | |
| (SEQ ID NO:22) IMG410: | ACAGTCGACGATACGTTCTCACCCAGTCTCC | |
| (SEQ ID NO:20) IMG411: | CCAAGCTCCACCAGCTGTACATCGGCTTTTGTCACAGGG | |

TABLE 6-continued (SEQ ID NO:21) IMG412: GAATCTAGATTATCATGAGGAGACGGTG (SEQ ID NO:1) CtxUp: GTGTGTGATACGAAACGAAGCATTGGATCCTAGAAGTGAAACGGGGTTTACCG (SEQ ID NO:2) CtxLo: GTTTTCCCAGTCACGACGACGTTGTAAAACGACAGAATCTGCCCGATATAACTTATC (SEQ ID NO:3) CtxΔSig: CAGCACGTTGTAGTACTACCTTTACCATATA

---

We claim:

1. An isolated replicon comprising DNA which encodes a fusion protein, said protein comprising:
   a) a ToxR regulatory domain,
   b) a transmembrane domain, and
   c) the variable immunoglobulin domain of a Bence-Jones REI protein.

2. The replicon of claim 1, wherein the transmembrane domain comprises the transmembrane helix of the ToxR gene of *Vibrio cholerae*.

* * * * *